US012583886B2

(12) United States Patent (10) Patent No.: US 12,583,886 B2
Raducanu et al. (45) Date of Patent: Mar. 24, 2026

(54) SLIDING CLAMP-BASED AFFINITY PURIFICATION SYSTEMS, METHODS OF MAKING AND USE THEREOF

(71) Applicant: King Abdullah University of Science and Technology, Thuwal (SA)

(72) Inventors: Vlad-Stefan Raducanu, Thuwal (SA); Muhammad Tehseen, Thuwal (SA); Fahad Rashid, Thuwal (SA); Samir M. Hamdan, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 1104 days.

(21) Appl. No.: 17/415,600

(22) PCT Filed: Dec. 20, 2019

(86) PCT No.: PCT/IB2019/061232
§ 371 (c)(1),
(2) Date: Jun. 17, 2021

(87) PCT Pub. No.: WO2020/129027
PCT Pub. Date: Jun. 25, 2020

(65) Prior Publication Data
US 2022/0081467 A1 Mar. 17, 2022

Related U.S. Application Data

(60) Provisional application No. 62/900,925, filed on Sep. 16, 2019, provisional application No. 62/857,531, filed on Jun. 5, 2019, provisional application No. 62/783,484, filed on Dec. 21, 2018.

(51) Int. Cl.
| | |
|---|---|
| C07K 1/22 | (2006.01) |
| B01D 15/38 | (2006.01) |
| C07K 1/04 | (2006.01) |
| C07K 14/47 | (2006.01) |

(52) U.S. Cl.
CPC ............ *C07K 1/22* (2013.01); *B01D 15/3809* (2013.01); *C07K 1/042* (2013.01); *C07K 14/4738* (2013.01)

(58) Field of Classification Search
CPC ...... C07K 1/22; C07K 1/042; C07K 14/4738; B01D 15/3809
See application file for complete search history.

(56) References Cited

U.S. PATENT DOCUMENTS

2017/0137467 A1* 5/2017 Rothbauer ............. C12N 15/62

FOREIGN PATENT DOCUMENTS

| | | |
|---|---|---|
| WO | 2004053460 | 6/2004 |
| WO | 2014046278 | 3/2014 |
| WO | 2017201105 | 11/2017 |

OTHER PUBLICATIONS

Chen et al (2012, Available Online: Jul. 3, 2012, Advanced Drug Delivery Reviews, doi.org/10.1016/j.addr.2012.09.039) {herein Chen}. (Year: 2012).*
Fairhead et al (2015, Date Published: Jul. 1, 2015, Methods Mol Biol., doi:10.1007/978-1-4939-2272-7_12) {herein Fairhead}. (Year: 2015).*
Bieniossek, et al., "MultiBac: multigene baculovirus-based eukaryotic protein complex production", Curr. Protoc. Protein Sci., Chapter 5, Unit 5.20 (2008).
Dalrymple, et al., "A universal protein-protein interaction motif in the eubacterial DNA replication and repair systems", PNAS, 98(20):11627-11632 (2001).
De Biasio, et al., "Structure of p15(PAF)-PCNA complex and implications for clamp sliding during DNA replication and repair", Nature Communications, 6:6439 (2015).
Dieckman, et al., "PCNA structure and function: insights from structures of PCNA complexes and post-translationally modified PCNA", Subcell Biochem., 62:281-299 (2012).
Dojima, et al., "Comparison of the efficiencies of different affinity tags in the purification of a recombinant secretory protein expressed in silkworm larval hemolymph", Biotechnology and Bioprocess Engineering, 14(3):281-287 (2009).
Dovrat, et al., "Sequential switching of binding partners on PCNA during in vitro Okazaki fragment maturation", PNAS, 111(39):14118-14123 (2014).
Duan, et al., "Quantification of the affinities and kinetics of protein interactions using silicon nanowire biosensors", Nature Nanotechnology, 7(6):401-407 (2012).
Escoffre, et al., "In-Vivo Gene Delivery by Sonoporation: Recent Progress and Prospects", Curr. Gene Ther., 13(1):2-14 (2013).
Gerik, et al., "Overproduction and Affinity Purification of *Saccharomyces cerevisiae* Replication Factor C", J. Biol. Chem., 272(2):1256-1262 (1997).
Gibson, et al., "Chemical synthesis of the mouse mitochondrial genome", Nature Methods, 7(11):901-903 (2010).
Gomes, et al., "Two modes of FEN1 binding to PCNA regulated by DNA", EMBO Journal, 19(14):3811-3821 (2000).
Guan, et al., "Challenges and recent advances in affinity purification of tag-free proteins", Biotechnology Letters, 36(7): 1391-1406 (2014).
Hedglin, et al., "Monitoring the Retention of Human Proliferating Cell Nuclear Antigen at Primer/Template Junctions by Proteins That Bind Single-Stranded DNA", Biochemistry, 56:3415-3421 (2017).
Hedglin, et al., "Stepwise assembly of the human replicative polymerase holoenzyme", Elife, 2: e00278 (2013).

(Continued)

*Primary Examiner* — Erica Nicole Jones-Foster
(74) *Attorney, Agent, or Firm* — Pabst Patent Group LLP

(57) ABSTRACT

Described are affinity purification system that includes a carrier/surface that is non-cellular, and sliding clamp (SC) protein, and methods for purifying proteins that bind to the SC. The SC is associated with the carrier/surface via covalent/non-covalent interactions. To attain control of coupling site, the SC can be mutated via site-directed mutagenesis to introduce an exogenous residue and, the exogenous internal residue is conjugated to the non-cellular surface through the linker. The SC can also be coupled to the carrier via non-covalent interactions such as the affinity interactions involved in ligand/binding partner complex formation. The SC-based affinity purification system are used in a purification column as bait proteins, to isolate SC binding partners or non SC-binding proteins engineered to contain a SC binding site prior to its purification.

30 Claims, 13 Drawing Sheets

Specification includes a Sequence Listing.

(56)                    References Cited

OTHER PUBLICATIONS

Hedglin, et al., "Stability of the human polymerase o holoenzyme and its implications in lagging strand DNA synthesis", PNAS, 113(13):E1777-E1786 (2016).

Iwata, et al., "Dissecting the interactions of Serrate with RNA and Dicer-Like 1 in *Arabidopsis* microRNA precursor processing", Nucleic Acids Res., 41(19):9129-9140 (2013).

Kalambet, et al., "Reconstruction of chromatographic peaks using the exponentially modified Gaussian function", Journal of Chemometrics, 25:352-356 (2011).

Kimple, et al., "Overview of Affinity Tags for Protein Purification", Current Protocols in Protein Science, 73: Unit-9.9 (2013).

Koniev, et al., "Developments and recent advancements in the field of endogenous amino acid selective bond forming reactions for bioconjugation", Chemical Society Reviews, 44(15):5495-5551 (2015).

Kumar, et al., "Stepwise loading of yeast clamp revealed by ensemble and single-molecule studies", PNAS, 107(107):19736-19741 (2010).

Li, et al., "Novel system for in vivo biotinylation and its application to crab antimicrobial protein scygonadin", Biotechnol. Lett., 34(9):1629-1635 (2012).

Maga, et al., "Proliferating cell nuclear antigen (PCNA): a dancer with many partners", Journal of Cell Science, 116(Pt 15):3051-3060 (2003).

Mailand, et al., "Regulation of PCNA—protein interactions for genome stability", Nature Reviews: Molecular Cell Biology, 14(5):269-282 (2013).

Majka, et al., "The PCNA-RFC families of DNA clamps and clamp loaders", Progress in Nucleic Acid Research and Molecular Biology, 78(78):227-260 (2004).

Masuda, et al., "Different types of interaction between PCNA and PIP boxes contribute to distinct cellular functions of Y-family DNA polymerases", Nucleic Acids Res., 43(16):7898-7910 (2015).

Miller, et al., "Targeted vectors for gene therapy", FASEB J., 9(2):190-9 (1995).

Moldovan, et al., "PCNA, the maestro of the replication fork", Cell, 129(4):665-679 (2007).

Muhammad, et al., "Proliferating cell nuclear antigen-agarose col. A tag-free and tag-dependent tool for protein purification affinity chromatography", Journal of Chromatography A, 1602:341-349 (2019).

Ohta, et al., "A proteomics approach to identify proliferating cell nuclear antigen (PCNA)-binding proteins in human cell lysates. Identification of the human CHL12/RFCs2-5 complex as a novel PCNA-binding protein", J. Biol. Chem., 277(43):40362-40367 (2002).

Rashid, et al., "Initial state of DNA-Dye complex sets the stage for protein induced fluorescence modulation", Nat. Commun., 10(1):2104 (2019).

Sakurai, et al., "Structural basis for recruitment of human flap endonuclease 1 to PCNA", Embo Journal, 24(4):683-693 (2005).

Schmidt, et al., "Development of the Twin-Strep-tag® and its application for purification of recombinant proteins from cell culture supernatants", Protein Expression and Purification, 92(1):54-61 (2013).

Schwarzenberger, et al., "Targeted gene transfer to human hematopoietic progenitor cell lines through the c-kit receptor", Blood, 87(2):472-478 (1996).

Slade, "Maneuvers on PCNA Rings during DNA Replication and Repair", Genes, 9(8):416 (2018).

Soofiyani, et al., "Gene therapy, early promises, subsequent problems, and recent breakthroughs", Advanced Pharmaceutical Bulletin, 3(2):249-255 (2013).

Strzalka, et al., "Proliferating cell nuclear antigen (PCNA): a key factor in DNA replication and cell cycle regulation", Annals of Botany, 107(7):1127-1140 (2011).

Tehseen, et al., "Proliferating cell nuclear antigen-agarose column: A tag-free and tag-dependent tool for protein purification affinity chromatography", J. of Chromatography A, 1602:341-349 (2019).

Verma, et al., "Gene therapy: twenty-first century medicine", Annu. Rev. Biochem., 74:711-38 (2005).

Warbrick, "PCNA binding through a conserved motif", Bioessays, 20(3):195-199 (1998).

Zhao, et al., "Three novel high performance affinity chromatographic media for the separation of antithrombin III from human plasma", Biomedical Chromatography, 15(8):487-492 (2001).

Zhang, et al., "Advancement and prospects of tumor gene therapy", Chinese J. Cancer Res., 30(3):182-8 (2011).

Zhu, et al., "Post-translational modifications of proliferating cell nuclear antigen: A key signal integrator for DNA damage response (Review)", Oncology Letters, 7(5):1363-1369 (2014).

International Search Report for corresponding PCT application PCT/IB2019/061232 dated Jun. 9, 2020.

* cited by examiner

HisTrap    PCNA-Agarose    Gel Filtration

Elution    Elution    Elution

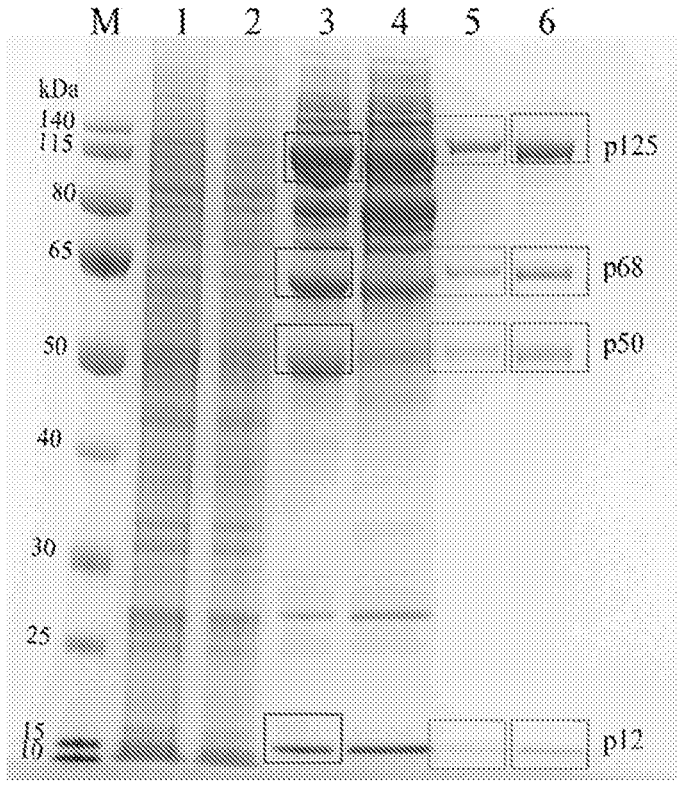
FIG. 2B
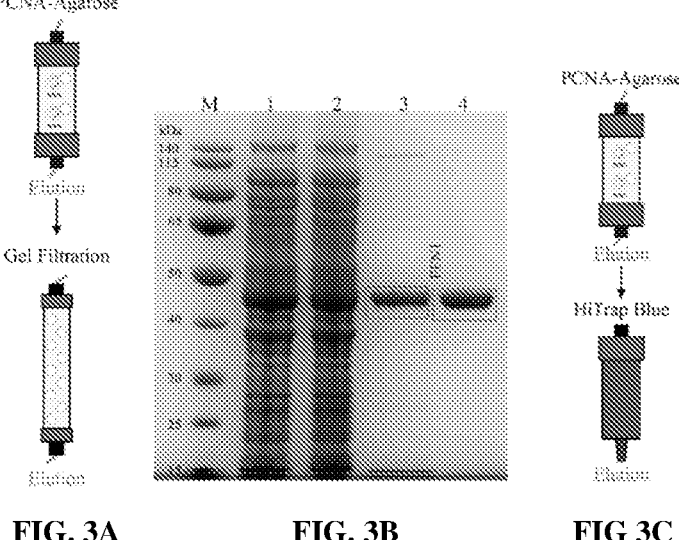
FIG. 3A                    FIG. 3B                    FIG 3C

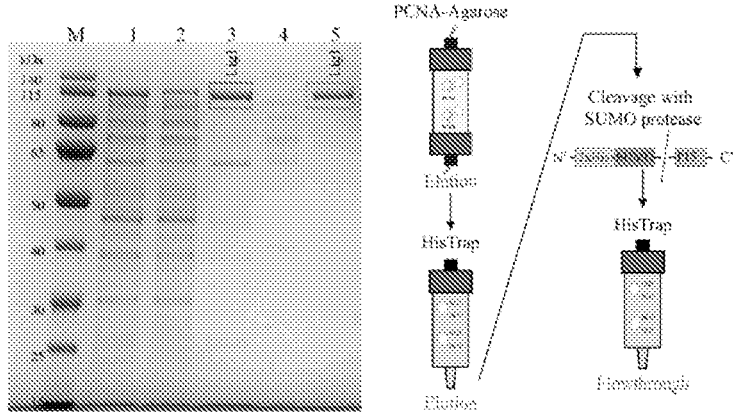
FIG. 3D                                    FIG. 3E
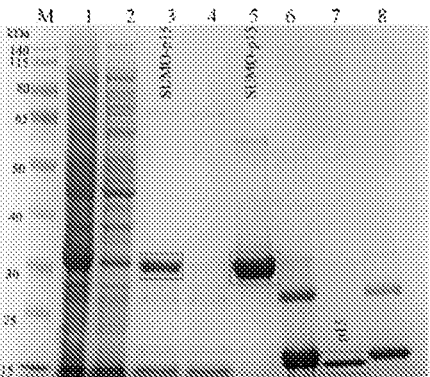
FIG. 3F
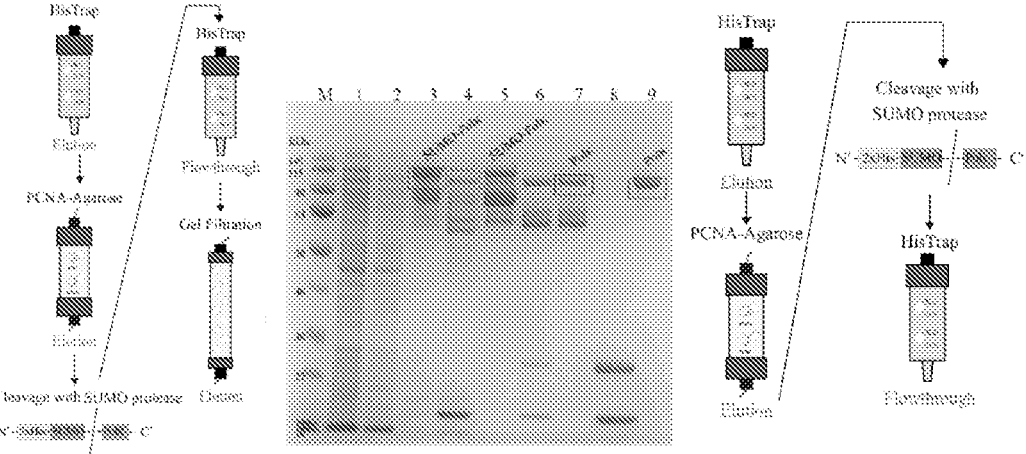
FIG. 4A                    FIG. 4B                    FIG. 4C

FIG. 4D                    FIG. 4E

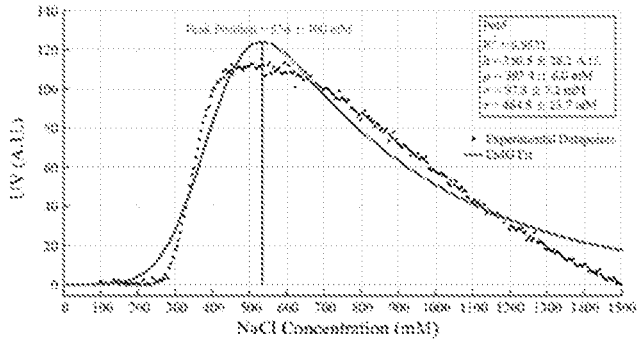
FIG. 7G
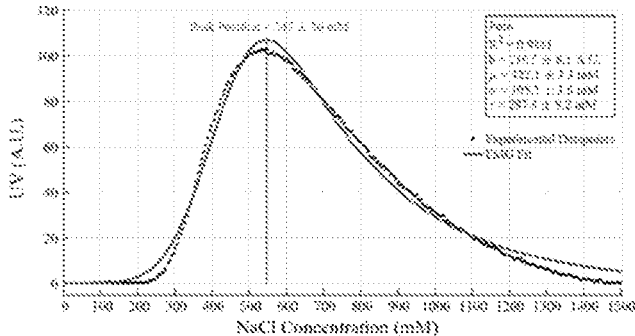
FIG. 7H
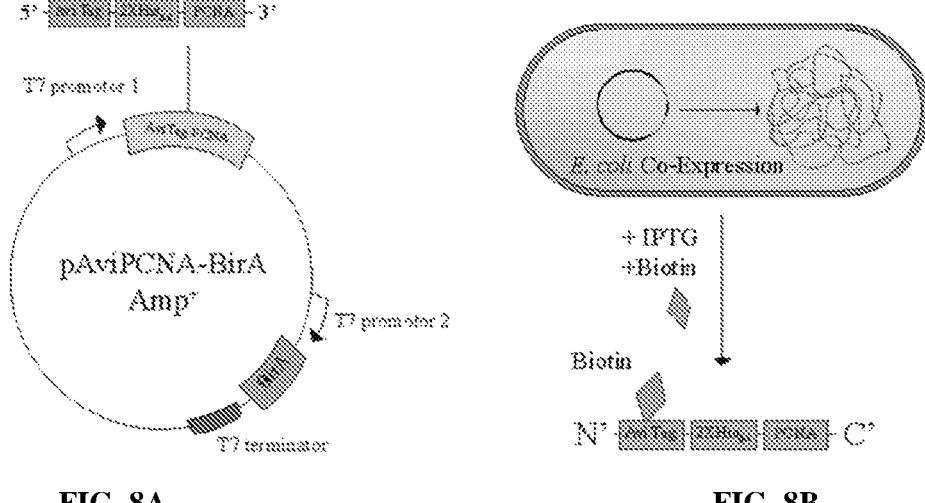
FIG. 8A                                              FIG. 8B

SLIDING CLAMP-BASED AFFINITY PURIFICATION SYSTEMS, METHODS OF MAKING AND USE THEREOF

CROSS-REFERENCE TO RELATED APPLICATIONS

The present application is a National Phase application under 35 U.S.C. § 371 of International Application No. PCT/IB2019/061232, filed on Dec. 20, 2019, which claims priority to U.S. Applications No. 62/783,484, filed Dec. 21, 2018, 62/857,531 filed Jun. 5, 2019, and 62/900,925, filed Sep. 16, 2019, the disclosures of which are incorporated herein by reference in their entirety.

REFERENCE TO SEQUENCE LISTING

The Sequence Listing submitted as a file named "KAUST_2019_037_05_371_ST25.txt", created on Jan. 20, 2025, and having a size of 10,263 bytes is hereby incorporated by reference pursuant to 37 C.F.R. § 1.823 (b) (1).

FIELD OF THE INVENTION

The disclosed invention is generally in the field of protein affinity systems, particularly protein affinity columns containing a non-cellular surface and a fusion protein, such as proliferating cell nuclear antigen (PCNA), where the fusion protein is covalently or non-covalently conjugated to the non-cellular surface, preferably via a linker using an internal residue of the fusion protein or a tag linked to the protein.

BACKGROUND OF THE INVENTION

Chromatography is an important biochemical technique widely used for purification of different proteins and peptides. Several different strategies have been developed to purify proteins on a large scale. These include affinity, size exclusion, hydrophobic interaction, ion exchange, etc. Affinity chromatography commonly involves fusing a small peptide tag, like FLAG-, poly-His-, c-myc-, and Strep-tag at the N- or C-terminus of the target protein, i.e., protein of interest. However, the importance of N-or C-terminus of the protein in interaction could be big hurdle in using these tags. Tags introduce extraneous amino acids at the N- or C-terminus, which can interfere with the protein's interactions with other proteins or with the function of the protein. In some proteins, these extraneous amino acids when introduced and left at the N-terminus dramatically decrease the protein's activity, such as by 50-folds. Further, some applications, such as crystallization and antibody production, may require cleavage or removal of these tags. Cleavage can introduce problems such as secondary cleavage of target protein resulting in the retrieval of incomplete target protein; high cost of proteases; and difficult optimization conditions. Further, affinity tags are often purified under conditions that can affect the protein.

Ohta, et al., J. Biol. Chem. 2002, 277 (43), 40362-40367 and Gerik, et al., *J. Biol. Chem.* 1997, 272 (2), 1256-1262 have described coupling native proliferating cell nuclear antigen (PCNA) to Affi-Gel 15 beads and Affi-Gel 10 beads, respectively, to purify proteins. However, these involve N-terminus N-hydroxysuccinimide (NHS) ester coupling. In some instances, it may be desirable to avoid NHS ester coupling that is very selective for primary amines. For example, in human PCNA, lysine 164 (i.e., a primary amine) is highly solvent exposed and extremely important for ubiquitination of the PCNA. Non-specific NHS-coupling of this lysine would block the ubiquitination of the PCNA (Zhu, et al., Oncology letters 2014, 7 (5), 1363-1369). Ubiquitination can be an important aspect in scenarios where a target protein only interacts with an ubiquinated protein (such as PCNA) used for isolating the target protein. In addition, many of the surface exposed lysine residues in PCNA have very important functions either on their own or in motifs that affect PCNA structure-function relationship. Further, with respect to N-terminus labelling, in some DNA clamps, the N-terminus may be inaccessible to the resin active chemical group and, therefore, the efficiency of labeling would be reduced. Moreover, restricting the coupling to NHS N-terminal can immobilize proliferating cell nuclear antigen (PCNA), in a certain geometrical orientation that can prevent its interacting partners from binding. Accordingly, there remains a need to develop affinity systems that circumvent the above-mentioned problems.

Therefore, it is an object of the invention to provide an affinity system with improved properties.

It is also an object of the invention to provide an affinity system with improved properties for protein purification.

It is also an object of the invention to provide an affinity system with improved properties for protein purification, which contains a fusion peptide from a protein as the bait molecule.

It is also an object of the invention to provide an affinity system with improved properties for protein purification, which uses DNA clamp proteins.

It is also an object of the invention to provide an affinity system with improved properties for protein purification, which contains proliferating cell nuclear antigen as the bait molecule.

SUMMARY OF THE INVENTION

Described are affinity purification system that includes a carrier/surface that is non-cellular, herein, "carrier", and sliding clamp (SC) such as PCNA (proliferating cell nuclear antigen) protein, herein, sliding SC-based affinity purification system, and methods for purifying proteins that bind to the SC. The SC is associated with the carrier/surface via covalent or non-covalent interactions to couple the SC to the carrier/surface.

In one embodiment, the SC affinity purification system is a carrier, a sliding clamp protein such as PCNA (proliferating cell nuclear antigen) protein, and a linkage chemistry (e.g. linker). The SC is covalently coupled to the carrier via the linkage chemistry (e.g. linker), and is designed for control of the site of coupling of the SC, to the linker. In this embodiment, coupling of the SC to the carrier does not involve its N-terminal or C-terminal sequence. In a particularly preferred embodiment, the SC is PCNA, and coupling of the PCNA protein/polypeptide does not involve N-terminus N-hydroxysuccinimide (NHS) ester coupling.

In order to attain control of coupling site, the SC is mutated via site-directed mutagenesis to introduce an exogenous residue such as a cysteine residue and, the exogenous internal residue is conjugated to the non-cellular surface through the linker. A preferred linker contains a thioether bond, or both a thioether bond and an amide bond, when the introduced residue is cysteine. A preferred functional group is an iodoacetyl group, and the linker can range in size from 3-20 atoms, preferably, between 8-14 atoms. The sulfhydryl group reacts with the iodoacetyl group to form a stable thioether bond.

The SC preferably is human PCNA, and the internal residue introduced via site directed mutagenesis is cysteine at position 107 of PCNA occupied by asparagine in a wild-type PCNA, i.e, a N107C mutation; and the linker contains a thioether bond, or both a thioether bond and an amide bond. A preferred non-cellular surface is an agarose bead. In a preferred embodiment, the SC is linked to an agarose bead by a linker, functionalized for interaction with sulfhydryl groups.

In another embodiment, the affinity purification system contains a carrier, and a sliding clamp protein such as PCNA (proliferating cell nuclear antigen) protein, with the clamp protein coupled to the carrier via non-covalent interactions. The noncovalent interactions is preferably provided by the affinity interactions involved in ligand/binding partner (herein, ligand/receptor or receptor/ligand) complex formation. Thus, in this embodiment, the SC is engineered/ modified to bind a ligand or its binding partner, and the carrier is modified to include the ligand or its binding partner, such that the SC and carrier are kept in contact as a result of complex formation between the ligand and its binding partner. A preferred ligand/receptor pair includes biotin and a biotin binding compound.

The SC affinity purification systems are used in a purification column as bait proteins, to isolate target binding partners, for example, proteins that bind the SC, directly, or indirectly. In embodiments where the protein does not bind the clamp protein directly (non-SC binding protein), the non SC-binding protein is engineered to contain a SC binding site prior to its purification.

BRIEF DESCRIPTION OF THE DRAWINGS

FIGS. 1A and 1B show coupling of PCNA to various resins. FIG. 1A is a schematic illustration of irreversible coupling of PCNA (N107C-PCNA) with SulfoLink Coupling resin. Model of human PCNA was generated using UCSF Chimera from PDB code 1AXC(Gulbis, et al., Cell 1996, 87, 297-306). PCNA subunits are shown in ribbon form in green, yellow and blue. The asparagine 107 residue mutation to cysteine is shown in red for one PCNA monomer. FIG. 1B is a bar chart illustrating the percentage of flow-through, wash and bound fractions of PCNA immobilized through various non-covalent (via Flag and Strep tag) and covalent (via NHS and SulfoLink) chemistries. All percentages were calculated from an initial protein amount of 24 mg PCNA and the coupling was performed on 1 ml of each resin as described in the examples below section. For each triplet of columns in FIG. 1B, data are shown in the following order from left to right: Flow through, Wash, and Bound.

FIGS. 2A and 2B show purification of human recombinant Polδ from Sf9 insect cells. FIG. 2A is a schematic of the procedure employed for the purification of Polδ. FIG. 2B is an SDS-PAGE gel image showing different steps of purification: Lane 1, lysate; lane 2, flow-through from HisTrap; lane 3, protein eluted from HisTrap; lane 4, flow-through from PCNA-Agarose column; lane 5, Polδ elution from PCNA-Agarose column; lane 6, Polδ after gel filtration. All protein fractions were separated on a 10% SDS-PAGE gel and stained with Coomassie blue. Size marker (M) (kDa) is on the left side of the gel.

FIGS. 3A-3F show purification of human recombinant FEN1, Lig1 and p15 from E. coli. FIG. 3A is a schematic of the procedure employed for the purification of FEN1. FIG. 3B is an image of an SDS-PAGE gel showing the different steps of purification: Lane 1, lysate; lane 2, flow-through from PCNA-Agarose column; lane 3, FEN1 elution from PCNA-Agarose column; lane 4, FEN1 after gel filtration. FIG. 3C is a schematic of the procedure employed for the purification of Lig1. FIG. 3D is an image of an SDS-PAGE gel showing the different steps of purification: Lane 1, lysate; lane 2, flow-through from PCNA-Agarose column; lane 3, Lig 1 elution from PCNA-Agarose column; lane 4, flow-through from HiTrap Blue, lane 5, lig1 after HiTrap Blue elution. FIG. 3E is a schematic of the procedure employed for the purification of p15. FIG. 3F is an image of an SDS-PAGE gel showing the different steps of purification: Lane 1, lysate; lane 2, flow-through from PCNA-Agarose column; lane 3, p15 eluted from PCNA-Agarose column; lane 4, flow-through from HisTrap; lane 5, p15 eluted from HisTrap; lane 6, p15 after SUMO protease digestion; lane 7, untagged p15 in flow-through from HisTrap; lane 8, proteins eluted from HisTrap containing SUMO protease. All proteins were separated on a 10% SDS-PAGE gel and stained with Coomassie blue. Size markers (M) (kDa) are on the left side of each gel.

FIGS. 4A-4F show purification of human recombinant translesion DNA polymerases (Polk, Polt, Poln) from E. coli. FIG. 4A is a schematic of the procedure employed for the purification of Polk. FIG. 4B is an image of an SDS-PAGE gel showing the different steps of purification: Lane 1, lysate; lane 2, flow-through from HisTrap; lane 3, Polk eluted from HisTrap; lane 4, flow-through from PCNA-Agarose column; lane 5, Polk eluted from PCNA-Agarose column; lane 6, Polk after SUMO protease digestion; lane 7, untagged Polk in flow-through from HisTrap; lane 8, proteins eluted from HisTrap containing SUMO protease; lane 9, Polk after gel filtration. FIG. 4C is a schematic of the procedure employed for the purification of Polt. FIG. 4D is an image of an SDS-PAGE gel showing the different steps of purification: Lane 1, lysate; lane 2, flow-through from HisTrap; lane 3, Polt eluted from HisTrap; lane 4, flow-through from PCNA-Agarose column; lane 5, Polt eluted from PCNA-Agarose column; lane 6, Polt after SUMO protease digestion; lane 7, untagged Polt in flow-through from HisTrap; lane 8, proteins eluted from HisTrap containing SUMO protease. FIG. 4E is a schematic of the procedure employed for the purification of Poln. FIG. 4F is an image of an SDS-PAGE gel showing the different steps of purification: Lane 1, lysate; lane 2, flow-through from HisTrap; lane 3, Poln eluted from HisTrap; lane 4, Poln after SUMO protease digestion; lane 5, untagged Poln in flow-through from HisTrap; lane 6, proteins eluted from HisTrap containing SUMO protease; lane 7, flow-through from PCNA-Agarose column; lane 8, Poln eluted from PCNA-Agarose column. All proteins were separated on a 10% SDS-PAGE gel and stained with Coomassie blue. Size markers (M) (kDa) are on the left side of each gel.

FIG. 5A is a schematic representation of recombinant PIPP21-Tus expression construct. FIG. 5B is a schematic of the procedure employed for the purification of PIPP21-Tus. FIG. 5C is an image of an SDS-PAGE gel showing the different steps of purification: Lane 1, lysate; lane 2, flow-through from HisTrap; lane 3, Tus eluted from HisTrap; lane 4, flow-through from PCNA-Agarose column; lane 5, Tus elution from PCNA-Agarose column; lane 6, Tus after SUMO protease digestion; lane 7, untagged Tus in flow-through from HisTrap; lane 8, proteins eluted from HisTrap containing SUMO protease. All protein fractions were separated on a 10% SDS-PAGE gel and stained with Coomassie blue. Size markers (M) (kDa) are on the left side of each gel.

FIG. 6A is a line plot of the cumulative elution percentage versus the NaCl concentration for each of the studied proteins. The cumulative elution percentage is obtained as described in the Examples section. The color of the curves corresponds to those indicated in the inset table. The horizontal dashed line (red) indicates 50% cumulative elution. The intersection of each cumulative elution percentage curve gives the median NaCl concentration of elution for each protein. The median values are recorded in the inset table. FIG. 6B show the corresponding concentrations of the maxima of the elution peaks for each studied protein as described in the Methods section. The values are obtained by fitting the elution peaks using the described EMG model (FIGS. 7A-7H). The vertical bars indicate the 95% confidence interval for the positions of the maxima of the elution peaks. The bars corresponding to the proteins known to contain a single PIP box (PIPP21-Tus, Lig1, FEN1, p15, and Polt) and multiple PIP boxes (Polη, Polδ, and Polk) are indicated.

FIGS. 7A-7H are line graphs showing fittings of the elution peaks of purified proteins from PCNA-Agarose column using the described EMG model. The values of the EMG parameters are recorded in the graphs together with their 95% confidence interval. The goodness of fit is indicated by the R2 value for each graph. The vertical red lines represent the positions of the maxima of the elution peaks as calculated from the fitting parameters based on the description given in the examples below. This value, together with the 95% confidence interval, is also reported above each peak. The fitted elution profiles are shown for the following proteins: PIPP21-Tus (FIG. 7A), Lig1 (FIG. 7B), FEN1 (FIG. 7C), p15 (FIG. 7D), Polt (FIG. 7E), Polη (FIG. 7F), Polδ (FIG. 7G), and Polk (FIG. 7H).

FIGS. 8A-8D show purification scheme, elements, and results for producing biotin-labeled AviTag™-PCNA from *E. coli.* FIG. 8A is a schematic of the plasmid pAviPCNA-BirA used to produce biotin-labeled AviTag™-PCNA in *E. coli.* FIG. 8B is a schematic of the procedure employed for the expression and in vivo biotinylation of AviTag-PCNA in *E. coli.* FIG. 8C is a schematic of the procedure employed for the purification of biotin-labeled AviTag™-PCNA and its coupling to High Capacity NeutrAvidin™ Agarose. FIG. 8D is an image of an SDS-PAGE gel showing the different steps of purification and coupling of AviTag™-PCNA to High Capacity NeutrAvidin™ Agarose: Lane 1, lysate; lane 2, flow-through from HisTrap; lane 3, AviTag™-PCNA elution from HisTrap; lane 4, flow-through from High Capacity NeutrAvidin™ Agarose, lane 5, AviTag™-PCNA bound to High Capacity NeutrAvidin™ Agarose.

FIG. 9A is a schematic of the procedure employed for the purification of Lig1 using the AviTag™-PCNA-Agarose column. FIG. 9B is an image of an SDS-PAGE gel showing the different steps of purification: Lane 1, lysate; lane 2, flow-through from AviTag-PCNA-Agarose column; lane 3, Lig1 elution from AviTag™-PCNA-Agarose column; lane 4, Lig1 after HiTrap Blue elution.

DETAILED DESCRIPTION OF THE INVENTION

Figure 1A:
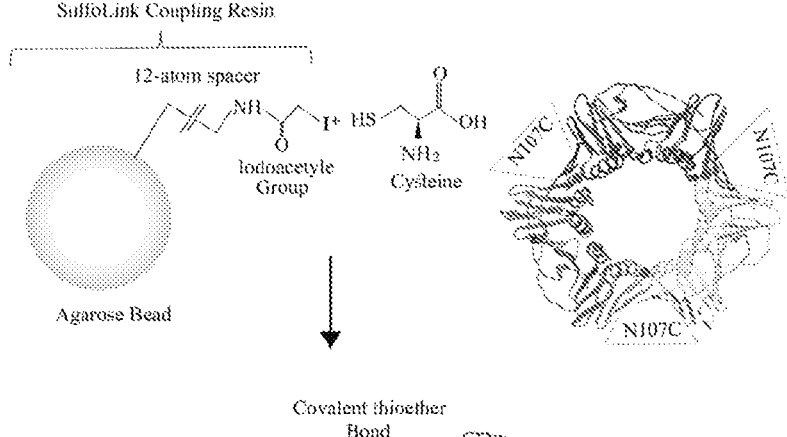
Figure 1A:
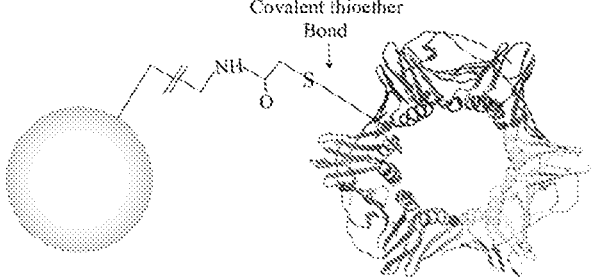

There is a continuous demand for the development of new chromatography-based protein purification strategies. Although affinity chromatography remains the most widely used strategy, its development has been focused on tag-dependent schemes. In these schemes, a small peptide tag, such as FLAG, poly-His and Strep, among others, is fused to the N-or C-terminus of the protein of interest to provide a broad purification strategy (for comparative reviews of the different tags refer to Lichty, et al., *Protein Expression and Purification* 2005, 41, 98-105; Kimple, et al., *Curr. Protoc. Protein Sci.* 2013, 73, Unit 9 9; Dojima, et al., *Biotechnology and Bioprocess Engineering* 2009, 14, 281-287). In other affinity chromatography strategies, a tag-free purification is used by relying on the interaction between the protein of interest and an antibody, a binding protein partner, or a substrate. However, the binding affinity in these tag-free strategies remains restricted to the protein of interest.

Clamp proteins such as PCNA are known and has been applied in analytic applications. As opposed to analytical application, however, PCNA must be coupled in a certain geometry to be accessible as much as possible for binding in order to maximize the efficiency of capturing the target protein, when used in purification applications. In analytical applications even short transient interactions may be suitable to detect the formation of a complex, while in protein purification relatively stable interactions are required to capture the maximum amount of the target proteins. For any given geometry via a given coupling chemistry/biochemistry, this accessibility has to be experimentally tested and cannot be predicted from known literature. Clamp protein-based affinity protein purification systems are provided, which employ covalent and non-covalent association of the clamp protein (exemplified by PCNA) to the a non-cellular carrier/surface.

A clamp protein-based (tag-free) affinity strategy which is applicable to more than one protein is provided herein in one embodiment, using sliding clamp (exemplified by PCNA) as a bait for purifying sliding clamp-binding proteins or non-sliding binding proteins engineered to bind a sliding clamp, wherein sliding is covalently attached to a non-cellular carrier surface. A sliding protein-based (using a tag) affinity strategy which is applicable to more than one protein is also provided herein in another embodiment, using sliding clamp (exemplified by PCNA) as a bait for purifying sliding clamp-binding proteins, or proetins engineered/modified to become sliding clamp binding, wherein sliding clapm is non-covalently attached to a non-cellular carrier surface.

I. Definitions

"Affinity interactions" as used herein refers to the combination of non-covalent interactions between a ligand and its binding partner to form a complex.

The term "amino acid" as used herein refers to a molecule containing both an amino group and a carboxyl group. Amino acids include alpha-amino acids and beta-amino acids. In certain forms, an amino acid is an alpha-amino acid. Amino acids can be natural or synthetic. Amino acids include, but are not limited to, the twenty standard or canonical amino acids: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). Common non-standard or non-canonical amino acids include, but are not limited to, selenocysteine, pyrrolysine, and N-formylmethionine.

The term "natural amino acid" as used herein refers to both the D-and L-isomers of the 20 common naturally occurring amino acids found in peptides (e.g., A, R, N, C, D, Q, E, G, H, I, L, K, M, F, P, S, T, W, Y, V (as known by the one letter abbreviations)).

The terms "synthetic amino acid", "non-natural amino acid" and "unnatural amino acid," are used interchangeably, and refer to an organic compound that has an amino group and a carboxyl group, and is not one of the D- and L-isomers of the 20 common naturally occurring amino acids found in peptides. Generally, it mimics the reactivity of a natural amino acid due to the presence of the amino and carboxyl groups. "Synthetic amino acid," "non-natural amino acid," or "unnatural amino acid" also refers to an amino acid that is not produced by an organism without genetic engineering. The synthetic amino acid as defined herein generally increases or enhances the properties of a peptide (e.g., selectivity, stability) when the synthetic amino acid is either substituted for a natural amino acid or incorporated into a peptide. "Synthetic amino acid," "non-natural amino acid," or "unnatural amino acid" can also refer to a natural amino acid whose side chain has been chemically modified to include a reactive group (e.g. alkyne; azide; alkene; tri-arylphosphine; aminooxy; carbonyl; hydrazide; sulfonyl chloride; maleimide; aziridine; —CN; acryloyl; acrylamide; sulfone; vinyl sulfone; cyanate; thiocyanate; isocyanate; isothiocyanate; alkoxysilane; dialkyl dialkoxysilane; diaryl dialkoxysilane; trialkyl monoalkoxysilane; vinyl silane; acetohydrazide; acyl azide; acyl halides; epoxide; glycidyl; carbodiimides; thiol; amine; phosphoramidate; vinyl ether; substituted hydrazine; an alkylene glycol bis(diester), e.g. ethylene glycol bis(succinate); thioester, e.g., alkyl thioester, α-thiophenylester, allyl thioester (e.g., allyl thioacetae, allyl thioproprionate); allyl ester (e.g., allyl acetate, allyl propionate); aryl acetate (e.g. phenacyl ester); orthoester; sulfonamide, e.g. 2-N-acyl nitrobenzenesulfonamide; vinyl sulfide; or a combination thereof) such that the resulting amino acid is structurally different from any of the 20 canonical naturally occurring amino acids.

"Bait", as relates to a protein, refers to a part of the protein that binds to a portion of a target molecule, such as another protein. Typically, target molecules interact with the bait via non-covalent linkage.

The term "biotin-binding" compound as used herein is intended to encompass any compound which is capable of tightly but non-covalently binding to biotin or any biotin compound.

"Conjugate", and its related terms, refers to the covalent or non-covalent linkage of a molecule to another molecule, or one part of a molecule to a different part of the same molecule. Similarly, the term "linkage chemistry" can refer to the type of linkage between, for example, a fusion protein such as sliding clamp protein/polypeptide and a carrier or surface. The linkage chemistry can involve covalent or non-covalent linkage. Covalent linkages can be direct or indirect (i.e., mediated via a linker). Non-covalent linkage includes electrostatic interactions, hydrogen bonding interactions, metal coordination, physical adsorption, host-guest interactions, hydrophobic interactions, π-stacking interactions, van der Waals interactions, magnetic interactions, and dipole-dipole interactions.

"Covalent linkage", refers to a bond or organic moiety that covalently links molecules (e.g. fusion proteins) to a non-cellular surface.

"Non-enzymatic protein" is a protein that binds to another molecule, and does not convert the molecule into a different molecule.

"Internal residue" as relates to a protein, refers to a residue that is neither the first nor last residue in the protein structure.

"Multimer", "multimeric," and related terms, as used herein in the context of proteins, refers to proteins that contain two or more evolutionary units called subunits. These proteins are generally referred to as multi-subunit proteins. Preferably, each subunit has a structured fold. The subunits can associate with each other via non-covalent linkage or via a covalent linkage. Each subunit can have an independent function or contribute to the function of the multimer in concert with other subunits. "Homo-multimeric" refers to a multi-subunit protein in which all the subunits have 100% sequence identity. "Hetero-multimeric" refers to a multi-subunit protein in which at least two of the subunits do not have 100% sequence identity.

"Non-cellular surface" refers to a surface that is not surrounding, or not in direct contact with, the cytoplasm of a living cell.

"PCNA" and "PCNA protein/polypeptide" are used interchangeably to refer to a proliferating cell nuclear antigen). "Sliding clamp," "sliding clamp protein," and "sliding clamp protein/polypeptide" are used interchangeably to refer to a sliding clamp protein.

As used herein, the term "polypeptide" refers to a chain of amino acids of any length, regardless of modification (e.g., phosphorylation or glycosylation).

"Surface" in the context of a non-cellular surface, refers to the exterior or outer boundary of a product. Generally, the surface or a surface of a product corresponds to the idealized surface of a three dimensional solid that is topologically homeomorphic with the product. The surface or a surface of the product can be an exterior surface or an interior surface of the product. An exterior surface forms the outermost layer of a product or device. An interior surface surrounds an inner cavity of a product, such as the inner cavity of a tube or bead. As an example, both the outside surface of a tube or bead and the inside surface of a tube or bead are part of the surface or a surface of the tube or bead. However, internal surfaces of the product that are not in topological communication with the exterior surface, such as a tube with closed ends, can be excluded as the surface or a surface of a product. Preferred surfaces are the outside surface and surfaces that can contact a sample containing a target molecule. Where the product is porous or has holes in its mean (idealized or surface, the internal faces of passages and holes would not be considered part of the surface or a surface of the product if its opening on the mean surface of the product is less than 5 nm.

As used herein, "transformed" and "transfected" encompass the introduction of a nucleic acid (e.g. a vector) into a cell by a number of techniques known in the art.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences. An "expression control sequence" is a DNA sequence that controls and regulates the transcription and/or translation of another DNA sequence.

II. Sliding Clamp based-Affinity Purification System

Described is an affinity purification system that allows for immobilization, in some embodiments, directed immobilization of sliding clamp proteins/polypeptides such as PCNA, designed for improved subsequent binding to, and purification of their binding partners. The affinity system can also be used to purify proteins that do not naturally interact with SC, by introducing into such proteins sliding clamp-interacting peptides (e.g. PCNA interacting peptides) as tags To improve and successfully develop a protein-based absorbent media for large scale protein purification two molecular and structural considerations have to be met: (1) The coupling method has to be efficient to capture large amount of the sliding clamp (for example, PCNA). In other words, the system has to be designed such that the tag or the amino acid where the coupling happens is well exposed and the chemistry/biochemistry of coupling has to be strong. Unless experimentally tested this cannot be known beforehand. There are lot of cases where a variety of tags do not bind to columns or bind inefficiently or the chemistry that is used is very sensitive or inefficient. The efficiencies of coupling via various methods are presented in FIG. 1B. Without careful design, prior art problems where the tags do not bind to columns or bind inefficiently or the chemistry that is used is very sensitive or inefficient will persist. (2) Once the clamp protein, for example, PCNA is coupled to the support media, in order successfully capture its binding partner (i.e., the target protein to be purified) it has to be immobilized in a certain geometry that allows the protein of interest to bind to it. There are two considerations here: first it has to be well oriented with respect to the beads to which it's attached so that the beads do not sterically hinder the binding and second, the coupling position should not block the binding sites themselves on clamp protein (for example coupling at a residue that is involved in the specific binding site). These parameters cannot be met without experimental testing.

Although various coupling techniques are known in the art, the present application discloses selection of coupling chemistries for using in making a clamp protein based column that meets the two criteria discussed above, can be for use in large scale protein purification.

Analytical applications vs. protein purification: The two molecular and structural considerations have to be met when using a sliding clamp protein for purification do not necessary apply for analytical applications. In analytical applications short transient interactions may be enough for detection and most often the efficiency is not considered (for example using an already purified protein in high amount) or cannot be controlled (for example in vivo detection). For analytical purposes the efficiency of coupling is very often inaccessible, not of interest or not mentioned.

The data in the present application demonstrates that without experimental testing one cannot predict the coupling efficiency (See FIG. 1B) even if the tag or the use of the tag was presented before for analytical purposes. For example, most of the presented tags (FIG. 1B) were used on PCNA for analytical applications. A usual timescale for protein purification from packing the column to purifying the interacting protein is in the order of hours. Most of the tags have off rates in the order of minutes. Thus, although the Strep tag may look like a good choice based on its application in other systems that did not use a clamp protein (Schmidt et al., *Protein Expression and Purification,* 92 (1) 54-61 (2013)

from the steady-state efficiency point of view (FIG. 1B) has an off-rate of about 10 minutes making it less desirable for coupling applications using clamp proteins such as PCNA.

Proof of concept is exemplified below using cysteine-iodoacetyl as covalent coupling chemistry and AviTag-Avidin as non-covalent coupling biochemistry. These systems show provide good stability, and high efficiency of coupling (FIG. 1B for cysteine-iodoacetyl with a value of ~85% and the text for AviTag-Avidin with a value of >90%). These efficacies could not be predicted from the art. Testing of these affinity columns with multiple target proteins illustrate that the method is general and PCNA is sufficiently exposed to capture different proteins that may have different binding modes and efficiencies. By purifying Lig1 over Sulfolink PCNA column (covalent coupling) and over Avi-Tag-Avidin PCNA column (no-covalent coupling) and demonstrating equivalent elution profiles, the data in this application application demonstrates that the two coupling methods though different both are efficient in exposing PCNA to capture the target protein.

Figures 1B, 2A:
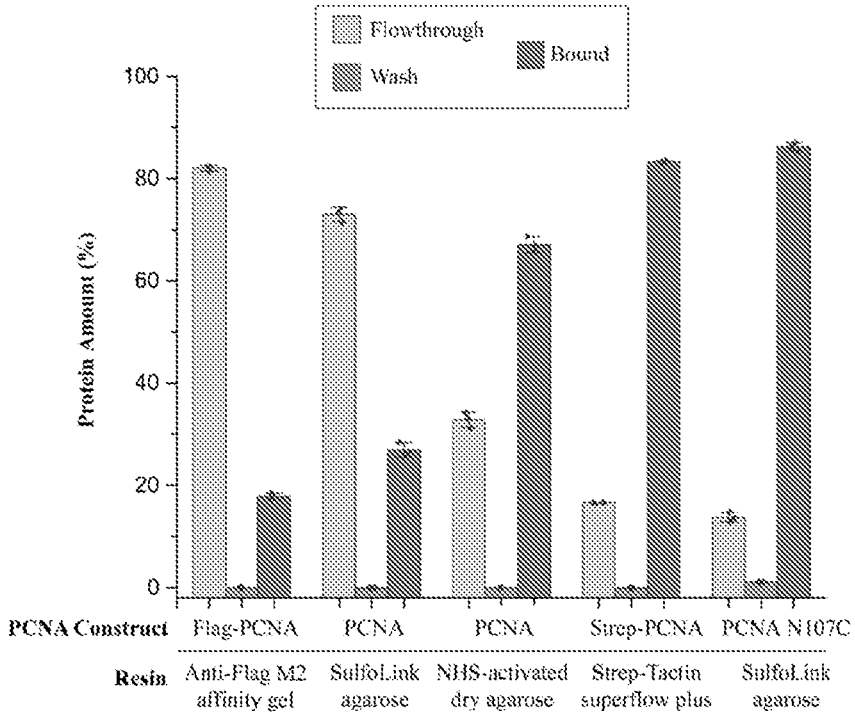

While FIG. 1B shows the steady state efficiency of coupling, i.e. the equilibrium at large time scale between on rate and off rate, this information is only half of the picture. In purification applications, from the moment when the column is packed onward, the column is continuously under flow. Therefore, the kinetic rates have to compete with the effect of the flow that naturally depletes the bait protein from the column. This depletion can be accelerated under elution buffer conditions that may include high salt, slight denaturing conditions, reducing agents and/or changes in pH. While a fast on-rate can help by rebinding the bait protein to the resin faster than the flow removes it, it is ideal to have a very slow off-rate that would prevent this effect from the beginning.

The irreversible coupling chemistry such as iodoacetyl-cysteine was selected since this coupling does not have an off rate and PCNA remains stably attached to the column.

The affinity system includes a Carrier or Surface which is non-cellular, sliding clamp protein/polypeptide (e.g. PCNA polypeptide/protein), and a linkage chemistry (e.g. linker). An internal residue of the PCNA protein/polypeptide is mutated to introduce an exogenous residue, preferably a cysteine residue and this exogenous internal residue is used as the site of conjugation to the carrier/surface, through the linkage chemistry (e.g. linker). The PCNA polypeptide/protein can be conjugated to the carrier or surface covalently or non-covalently. An advantage of the disclosed affinity system is that the site of conjugating the protein to the surface can be precisely controlled by virtue of controlling the site within the protein where the exogenous residue is introduced. Accordingly, topological and structural constraints, such as the requirement for labeling only N- and/or C-termini, are eliminated. More importantly, the site of inserting the exogenous residue can be selected such that conjugation of the PCNA polypeptide/protein does not occur on the same face to which the target protein or protein of interest binds.

The PCNA protein/polypeptide functions as a bait for a target molecule of interest. An advantage of the affinity system described herein, involves the option of not having to label the target molecule with an affinity tag. Accordingly, the protein-coupled column purification displays specificity, the target molecule can be retrieved in its native folded state and, thereby, retaining its activity.

Preferably, (i) the protein is a PCNA protein/polypeptide; (ii) the internal is residue introduced via site-directed mutagenesis; (ii) the internal residue introduced via site directed mutagenesis is cysteine; (iii) the linker contains a thioether bond, or a both thioether bond and an amide bond; (iv) site-directed mutagenesis is used to mutate a surface-exposed internal residue of PCNA protein/polypeptide, such as asparagine 107, i.e., N107; or combinations selected from (i), (ii), (iii), and (iv). Examples of combinations can be (i) and (ii); (i) and (iii); (i) and (iv); (i), (ii), and (iii); and (i), (ii), (iii), and (iv).

A. The Carrier or Surface

The carrier/surface is preferably a non-cellular surface and can be any of the commonly used materials for attaching bait molecules on to surfaces, and is preferably, not a cell (i.e., non-cellular). Useful materials that can serve as the non-cellular surface include materials to which a coupling or adhesion of a protein molecule is possible, such as for example glass surfaces, polysaccharides (agarose or sepharose beads, cellulose, cellulose acetate, dextran, nitrocellulose), plastic surfaces, such as polystyrene or polypropylene; other organic polymers such as polycarbonate, poly(methyl methacrylate) (PMMA), poly(acrylamide), poly(dimethyl siloxane), poly(ethylene oxide), poly(styrene acrylic acid), poly(styrene acrylate); filter materials, such as cellulose; silica; and silica-based superparamagnetic beads. Generally, the non-cellular carrier/surface contains a reactive group capable of reacting with another reactive group present in the PCNA protein/polypeptide or the PCNA protein/polypeptide coupled to a linker, to effect conjugation.

Covalent conjugation to the non-cellular carrier/surface can be performed by grafting molecules thereto. In some forms, prior to performing covalent conjugation, the carrier/surface can be modified by treating with plasma to introduce functional groups such as hydroxyl, carboxyl, ester, aldehyde, ketone, and carbonate, using, for example, oxygen plasma. In some forms, the carrier/surface can be treated using any other activation method known to one of skill in the art, to introduce other functional groups such as epoxy (glycidyl), amine, boronate, carbonyl imidazole, cyanate ester, etc. Preferably, compounds containing reactive functional groups can be reacted with these functional groups on the carrier/surface such that a reactive functional group is available to conjugate the protein to the surface. Preferably, the compounds containing the reactive functional groups will serve as the linkers.

The reactive group can be attached directly or indirectly to the non-cellular surface. Preferably, the reactive group is attached indirectly to the non-cellular surface via a linker. Preferably, the reactive group is an iodoacetyl group, for example a cysteine-iodoacetyl reaction and it provides a coupling efficiency of at least 70%, for example, up to 80%. Iodoacetyl-cysteine vs. NHS-amine coupling: Unlike NHS-amine coupling, iodoacetyl-cysteine attacks only cysteine residues (NHS can also attack critical Lysine residues), the position of the introduced cysteine can be controlled (NHS attacks primarily the N-terminal), it is not very sensitive to pH and resulted in much higher coupling efficiency (FIG. 1B).

In some forms, the reactive group is not NHS.

In some instances, NHS coupling may not be desirable, because hydrolysis of the ester competes with the coupling reaction, while pH affects the efficiency of the coupling reaction. For instance, the pH of the reaction solution and temperature can facilitate NHS ester hydrolysis by water (exhibiting half-lives of between 4 and 5 hours, 1 hour and 10 minutes at pH 7, 8 and 8.6, respectively (Koniev and Wagner, Chemical Society Reviews 2015, 44 (15), 5495-5551; Lim, et al., Langmuir 2014, 30 (43), 12868-12878). Human PCNA has an isoelectric point of 4.57. In order to maintain its stability and state of surface electric charge, a strong buffering reagent at neutral or slightly alkaline pH is required. Often this buffer is Tris based buffer. At normal buffer pH conditions required for NHS-coupling such as pH 7, often the used buffering reagent is based on primary amines such as Tris Buffer. Primary amine buffers such as Tris (TBS) are not compatible with NHS labelling, because they compete for reaction. At a larger scale the problem of pH may come into play while using sliding clamps from different organisms that have the isoelectric point close to the pH required for NHS-coupling. If this happens the protein loses its surface charge and it aggregates or denatures.

Preferably, the non-cellular surface contains a polysaccharide such as agarose.

In some forms, the sliding camp protein/polypeptide (e.g. PCNA protein/polypeptide) is non-covalently conjugated to the carrier or surface. Non-covalent linkage can be performed through interactions that include, but are not limited to, receptor-ligand complex formation and metal coordination.

B. Proteins

The affinity purification system disclosed herein employ proteins/polypeptides known as DNA clamps or sliding clamps. Sliding clamps are exemplified here using human PCNA protein. DNA clamp and sliding clamp are used herein interchangeably. The SC is used to purify a protein (herein target protein) that binds to the SC.

(i) DNA/Sliding Clamp

Sliding clamps are proteins that encircle double-stranded DNA and are found in all three domains of life. Although these proteins have different oligomeric states, they all possess a general pseudo-six-fold ring-shaped structure. Bacterial sliding clamps form homodimers, whereas archaeal and eukaryotic sliding clamps form homotrimers and heterotrimers. DNA clamps, such as PCNA, are evolutionarily well-conserved proteins found in a wide variety of diverse organisms including animals, yeast, and higher plants as well as in Archaea. Sequence, structure, and function conservation among various species and the large number of proteins they interact with make DNA clamps suitable baits to purify interacting partners.

PCNA is a dsDNA clamp that acts as a processivity factor for DNA polymerases and as a binding partner that supports and regulates the activities of many proteins during DNA replication, repair, and recombination (Moldovan, et al., *Cell* 2007, 129, 665-679; Strzalka and Ziemienowicz, *Annals of Botany* 2011, 107, 1127-1140; Majka, et al., Progress in Nucleic Acid Research and Molecular Biology 2004, 78 (78), 227-260). Most proteins use the PCNA interacting protein (PIP) motif to bind PCNA (Slade, Genes 2018, 9 (8), 416; Maga and Hubscher, *Journal of Cell Science* 2003, 116, 3051-3060; Warbrick, Bioessays 2000, 22, 997-1006). PCNA is a homo-trimeric ring-shaped protein (Dieckman, et al., *Subcell Biochem.* 2012, 62, 281-299) and therefore can bind up to three proteins at once (De Biasio, et al., Nature Communications 2015, 6, 6439; Sakurai, et al., *Embo Journal* 2005, 24, 683-693). DNA clamps, such as PCNA, are evolutionarily well-conserved proteins that are found in a wide variety of organisms including animals, yeast and higher plants, as well as archaea (Strzalka and Ziemienowicz, *Annals of Botany* 2011, 107, 1127-1140; Hedglin, et al., Cold Spring harbor Perspectives in Biology 2013, 5).

Eukaryotic PCNA is a homotrimer with each monomer composed of two similarly folded subunits connected by an inter-subunit-connecting loop. Subunit 1 is composed of residues 1 to 117, subunit 2 is composed of residues 135 to 258, and the inter-subunit-connecting loop is composed of residues 118 to 134. The human PCNA protein/polypeptide is a homo-trimeric ring-shaped polypeptide composed of 261 amino-acids and a molecular mass of 29 kDa for each subunit.

In some forms, the protein can be a recombinant protein. In some forms, the protein can be a wild-type protein or a mutant protein. Preferably, the protein is a mutant protein, i.e., produced via a mutated gene such that the protein contains an exogenous residue. The exogenous residue can be a residue that is not present in its corresponding position in a wild-type state of the protein and is, preferably, cysteine. By using a mutant protein, the site on the protein used to conjugate the protein to the non-cellular surface can be precisely controlled by virtue of controlling the site within the protein where the exogenous residue is introduced. In the case of the human PCNA protein/polypeptide the wild-type form does not contain any sufficiently solvent-exposed cysteine for conjugation. In some instances, a sufficiently solvent-exposed residue can be present in the wild-type, but conjugating the sliding clamp protein/polypeptide using this residue can lead to the occlusion of the site on the sliding clamp protein/polypeptide that possesses its bait properties for a given target molecule.

In some forms, a target protein does not interact with a sliding clamp protein/polypeptide (e.g. PCNA protein/polypeptide) in the absence of post-translational modification of the sliding clamp protein/polypeptide. (Zhu, et al., Oncology letters 2014, 7 (5), 1363-1369). Accordingly, in some forms, the sliding clamp protein/polypeptide (e.g. PCNA protein/polypeptide) contains a post-translational modification that includes, but is not limited to, ubiquitination, small ubiquitin-related modifier (SUMO), glycosylation, phosphorylation, and combinations thereof.

Typically, the protein is from eukaryotes, archaea, bacteria, viruses, or a combination thereof. Exemplary species from which the protein or gene coding the protein can be isolated include: *Homo sapiens, Macaca fascicularis, Macaca nemestrina, Rhinopithecus bieti, Gorilla gorilla gorilla, Nomascus, leucogenys, Mandrillus leucophaeus, Neovison vison, Ovis aries, Bos taurus, Rattus norvegicus, Oryza sativa, Mus musculus, Saccharomyces cerevisiae, Saccharolobus solfataricus, Pyrococcus furiosus, Archaeoglobus fulgibus, Thermococcus kodakarensis, Leishmania donovani, Sulfurisphaera tokodaii, Murine leukemia virus, Haloferax volcanii, Penaeus vannamei, Ricinus communis, Thermococcus gammatolerans, E. coli*, or a combination thereof.

Preferably, the protein or gene coding the protein is from a *Homo sapiens*, for example, MFEARLVQGS ILKKVL-EALK DLINEACWDI SSSGVNLQSM DSSHVSLVQLTLRSEGFDTY RCDRNLAMGV NLT-SMSKILK CAGNEDIITL RAEDNADTLA LVFEAPNQEK VSDYEMKLMD LDVEQLGIPE QEY-SCVVKMP SGEFARICRD LSHIGDAVVI SCAKDGVKFS ASGELGNGNI KLSQTSNVDK EEEAVTIEMN EPVOLTFALR YLNFFTKATP LSSTVTLSMS ADVPLVVEYK IADMGHLKYY LAPK-IEDEEGS (SEQ ID NO: 1; Uniprot entry 12004). In some forms, the protein contains the sequence MFEARLVQGSILKKVLEALKDLINEACWDISSS GVNLQSMDSSHVSLVQLTLRSEGFDTYRCDRN-LAMGVNLTSMSKIL KCAGNEDIITLRAEDNADTLA-LVFEAPCQEKVSDYEMKLMDLDVEQ LGIPEQEY-SCVVKMPSGEFARICRDLSHIGDAVVISCAKDGV-KFSASG ELGNGNIKLSQTSNVDKEEEAVTIEMNEP-VOLTFALRYLNFFTKATPL SSTVTLSMSAD-VPLVVEYKIADMGHLKYYLAPKIEDEEGS (SEQ ID NO: 5). SEQ ID NO: 5 is similar to SEQ ID NO: 1, but contains an N-terminal His-tag and N107C mutation.

The human PCNA mRNA sequence is shown below, GenBank: BC000491.2, transcript variant 1. This variant (1) represents the longer transcript. Variants 1 and 2 encode the same protein.

```
(SEQ ID NO: 2; NCBI Reference Sequence: NM_002592.2)
gcgtagcaga gtggtcgttg tctttctagg tctcagccgg tcgtcgcgac gttcgcccgc tcgctctgag gctcctgaag ccgaaaccag ctagactttc ctccttcccg cctgcctgta gcggcgttgt tgccactccg ccaccatgtt cgaggcgcgc ctggtccagg gctccatcct caagaaggtg ttggaggcac tcaaggacct catcaacgag gcctgctggg atattagctc cagcggtgta aacctgcaga gcatggactc gtcccacgtc tctttggtgc agctcaccct gcggtctgag ggcttcgaca cctaccgctg cgaccgcaac ctggccatgg gcgtgaacct caccagtatg tccaaaatac taaaatgcgc cggcaatgaa gatatcatta cactaagggc cgaagataac gcggatacct tggcgctagt atttgaagca ccaaaccagg agaaagtttc agactatgaa atgaagttga tggatttaga tgttgaacaa cttggaattc cagaacagga gtacagctgt gtagtaaaga tgccttctgg tgaatttgca cgtatatgcc gagatctcag ccatattgga gatgctgttg taatttcctg tgcaaagac ggagtgaaat tttctgcaag tggagaactt ggaaatggaa acattaaatt gtcacagaca agtaatgtcg ataaagagga ggaagctgtt accatagaga tgaatgaacc agttcaacta acttttgcac tgaggtacct gaacttcttt acaaaagcca ctccactctc ttcaacggtg acactcagta tgtctgcaga tgtacccctt gttgtagagt ataaaattgc ggatatggga cacttaaaat actacttggc tcccaagatc gaggatgaag aaggatctta ggcattctta aaattcaaga aaataaaact aagctctttg agaactgctt ctaagatgcc agcatatact gaagtctttt ctgtcaccaa
```

-continued

```
atttgtacct ctaagtacat atgtagatat tgttttctgt aaataaccta ttttttttctc tattctctgc aatttgttta aagaataaag tccaaagtca gatctggtct agttaaccta gaagtatttt tgtctcttag aaatacttgt gatttttata atacaaaagg gtcttgactc taaatgcagt tttaagaatt gttttttgaat ttaaataaag ttacttgaat ttcaaaaaaa aaaaaaaaaa a.
```

Transcript Variant: This variant (2) (NCBI Reference Sequence: NM_182649.1) differs in the 5' UTR compared to variant 1. Variants 1 and 2 encode the same protein.

NCBI Reference Sequence: NP_001233697.1; XP_021008112.1; NP_035175.1 (*Mus musculus*); XP_021405682.1; XP_018427627.1; and XP_018427627.1.

(SEQ ID NO: 3)
```
aacgcggcgc agggtgagag cgcgcgcttg cggacgcggc ggcattaaac ggttgcaggc gtagcagagt ggtcgttgtc tttctaggtc tcagccggtc gtcgcgacgt tcgcccgctc gctctgaggc tcctgaagcc gaaaccagct agactttcct ccttcccgcc tgcctgtagc ggcgttgttg ccactccgcc accatgttcg aggcgcgcct ggtccagggc tccatcctca agaaggtgtt ggaggcactc aaggacctca tcaacgaggc ctgctgggat attagctcca gcggtgtaaa cctgcagagc atggactcgt cccacgtctc tttggtgcag ctcaccctgc ggtctgaggg cttcgacacc taccgctgcg accgcaacct ggccatgggc gtgaacctca ccagtatgtc caaaatacta aaatgcgccg gcaatgaaga tatcattaca ctaagggccg aagataacgc ggataccttg gcgctagtat ttgaagcacc aaaccaggag aaagtttcag actatgaaat gaagttgatg gatttagatg ttgaacaact tggaattcca gaacaggagt acagctgtgt agtaaagatg ccttctggtg aatttgcacg tatatgccga gatctcagcc atattggaga tgctgttgta atttcctgtg caaaagacgg agtgaaattt tctgcaagtg gagaacttgg aaatggaaac attaaaattgt cacagacaag taatgtcgat aaagaggagg aagctgttac catagagatg aatgaaccag ttcaactaac ttttgcactg aggtacctga acttctttac aaaagccact ccactctctt caacggtgac actcagtatg tctgcagatg tacccccttgt tgtagagtat aaaattgcgg atatgggaca cttaaaatac tacttggctc ccaagatcga ggatgaagaa ggatcttagg cattcttaaa attcaagaaa ataaaactaa gctctttgag aactgcttct aagatgccag catatactga agtcttttct gtcaccaaat ttgtacctct aagtacatat gtagatattg ttttctgtaa ataacctatt ttttctcta ttctctgcaa tttgtttaaa gaataaagtc caaagtcaga tctggtctag ttaacctaga agtatttttg tctcttagaa atacttgtga tttttataat acaaagggt cttgactcta aatgcagttt taagaattgt ttttgaattt aaataaagtt acttgaattt caaacatca;
```
NCBI Reference Sequence: NM_182649.1).

In some forms, wherein the protein contains a peptide sequence according to SEQ ID NO: 1, or a variant thereof having between about 50% and about 100% sequence identity to SEQ ID NO: 1, or at least 80%, 85%, 90%, 95%, 96%, 97%, 98%, 99% sequence identity to SEQ ID NO: 1.

Representative examples of PCNA sequences which share at least 80% sequence identity with SEQ ID NO: 1 are represented by GenBank: AAX36355.1; ASR74820.1;

C. Conjugation (i) Covalent Linkage

The protein is conjugated to the non-cellular surface preferably covalent linkage mediated by a linker. The linker can range in size from 3-20 atoms, and is preferably, hydrophilic. In some forms, the linker is non-cleavable or cleavable. Preferably, linker is non-cleavable such that the protein is permanently attached to the non-cellular surface.

Preferably, the linker has the structure:

-X-Y-Ra-                                              Formula I wherein, (i) X contains between 3 and 90 atoms, inclusive, between 3 and 85 atoms, inclusive, between 3 and 80 atoms, inclusive, between 3 and 70 atoms, inclusive, between 3 and 60 atoms, inclusive, between 3 and 50 atoms, inclusive, between 3 and 40 atoms, inclusive, between 3 and 30 atoms, inclusive, between 3 and 20 atoms, inclusive, between 80 and 85 atoms, inclusive, or between 75 and 80 atoms, inclusive, preferably, X contains 10, 11, 12, 13, 14, and 15 atoms. Preferably, X can be an organic group such as substituted alkyl; unsubstituted alkyl; substituted alkylene; unsubstituted alkylene; a polyether, such as poly(ethylene glycol); substituted alkenyl; unsubstituted alkenyl; substituted alkynyl; unsubstituted alkynyl; or a combination thereof, such as unsubstituted alkylene and polyether. Preferably for these organic group, any of the number of atoms provided above, such as between 3 and 20;

(ii) Y is —NHC(O)—; —C(O)NH—; —C(O)O—; —OC (O)—; —O—; —NH—NHC(O)—; —OC(O)NH—; —NHC(O)O—; —C(O)—; —OC(O)O—; —S(=O$_2$)$_2$—; —S(=O)—; —S—; —N=N—; —N=CH—; a bond, such as a single bond, double bond, or triple bond; or absent; preferably, Y is —NHC (O)—; and (iii) Ra is a thioether, a substituted triazole (alkyne+azide "click" chemistry), a carbamate (amine+hydroxy using diimidazole carbonyl; or isocyanate+hydroxy), oxime ether (carbonyl+aminooxy), hydrazone (carbonyl+hydrazide), a carbonyl(ketone), imine (carbonyl+amine), sulfonamide (sulfonyl chloride+amine), azo (aromatic diazonium and anilines or phenols), dialkyl dialkoxysilane, diaryl dialkoxysilane, orthoester, acetal, aconityl, β-thiopropionate, phosphoramidate, trityl, vinyl ether, polyketal, or a combination thereof. The linker preferably includes a sulfhydryl reactive group. Sulfhydryl-reactive chemical groups include haloacetyls, maleimides, aziridines, acryloyls, arylating agents, vinylsulfones, pyridyl disulfides, TNB-thiols and disulfide reducing agents. Most of these groups conjugate to sulfhydryls by either alkylation (usually the formation of a thioether bond) or disulfide exchange (formation of a disulfide bond).

The most commonly used haloacetyl crosslinkers contain an iodoacetyl or a bromoacetyl group. Haloacetyls react with sulfhydryl groups at physiologic pH. The reaction of the iodoacetyl group proceeds by nucleophilic substitution of iodine with a sulfur atom from a sulfhydryl group, resulting in a stable thioether linkage. Using a slight excess of the iodoacetyl group over the number of sulfhydryl groups at pH 8.3 ensures sulfhydryl selectivity.

Pyridyl disulfides react with sulfhydryl groups over a broad pH range (the optimum is pH 4 to 5) to form disulfide bonds. During the reaction, a disulfide exchange occurs between the molecule's-SH group and the reagent's 2-pyridyldithiol group. The disulfide exchange can be performed at physiologic pH, because pyridyldithiol compounds form disulfide bonds with target sulfhydryls, conjugates prepared using these crosslinkers are cleavable with familiar disulfide reducing agents, such as dithiothreitol (DTT) or sample buffer for protein electrophoresis (SDS-PAGE). This chemistry can be used to create a reversible sulfhydryl immobilization resin.

In some forms, the linker contains a thioether. In some forms, the linker contains both a thioether and an amide. Linkers which are modified for specific binding to thiol groups for example, are known in the art. For example, iodoactyl linker for binding to agarose beads, or thiol (for example, 2-pyridyl disulfide)/iodoacetyl activated linkers used to produce thiol/iodoacetyl activated magnetic beads.

Every carrier/surface, protein, linker, X, Y, and Ra within the above definition is intended to be and should be considered to be specifically disclosed herein. Further, every subgroup that can be identified within the above definition is intended to be and should be considered to be specifically disclosed herein. As a result, it is specifically contemplated that any carrier/surface, protein, linker, X, Y, and Ra can be either specifically included for or excluded from use or included in or excluded from a list of carrier/surface, protein, linker, X, Y, and Ra. For example, any one or more of the carrier/surface, protein, linker, X, Y, and Ra described herein, with a structure depicted herein, or referred to in the Examples herein can be specifically included, excluded, or combined in any combination, in a set or subgroup of such carrier/surface, protein, linker, X, Y, and Ra. Such specific sets, subgroups, inclusions, and exclusions can be applied to any aspect of the compositions and methods described here. For example, the following can be specifically included or excluded, as a group or individually, from any X, Y, and Ra per se, or any one or more of the disclosed methods, or combinations of these: (i) X having between 80 and 85 atoms, inclusive, or between 75 and 80 atoms, inclusive; (ii) X containing poly(ethylene glycol); (iii) X containing unsubstituted alkylene and poly(ethylene glycol); (iv) Ra being a substituted triazole; (v) Ra being a substituted succinimide; or (vi) a combination of (i)-(v), such as (ii) and (iv), (ii) and (v), and (iii) and (iv).

(ii) Non-Covalent Linkage

Non-covalent linkage can be carried out through electrostatic interactions, hydrogen bonding interactions, metal coordination, physical adsorption, host-guest interactions, hydrophobic interactions, π-stacking interactions, van der Waals interactions, magnetic interactions, and dipole-dipole interactions.

A preferred non-covalent linkage is provided by the affinity interactions involved receptor-ligand complex formation. Binding of a ligand to its binding partner can occur by intermolecular forces, such as ionic bonds, hydrogen bonds, hydrophobic interactions and Van der Waals forces. Thus, affinity interactions as used herein refers to the combination of non-covalent interactions between a ligand and its binding partner to form a complex.

The binding partner component or the ligand component can be used to modify the SC. In some embodiment, the SC can be expressed as a recombinant fusion protein which includes component that binds to the receptor or ligand. In some preferred embodiments the affinity purification system utilizing non-covalent linkage to conjugate the protein to the carrier further includes one or more linkers, for example, one or more glycine-serine linkers.

Some illustrative examples of binding receptor-ligand complex chemistries that can be employed are discussed herein. A preferred non-covalent linkage is obtained by affinity interactions in a receptor ligand complex, preferably, a biotin-biotin binding compound complex.

For the biotin-biotin-binding compound pair such as biotin-streptavidin or biotin-avidin (or NeutrAvidin) pair, biotin can be attached to the sliding clamp protein/polypeptide (e.g. PCNA protein/polypeptide) and streptavidin, avidin or NeutrAvidin may be attached to the carrier or surface, or vice versa. Biotin binds via affinity interactions to biotin-binding compounds, thereby non-covalently conjugating the sliding clamp protein/polypeptide (e.g. PCNA protein/polypeptide) to the carrier or surface. For the Strep-tag/Strep-Tactin® pair, Strep-tag can be attached to the sliding clamp protein/polypeptide (e.g. PCNA protein/polypeptide) and Strep-Tactin® beads are used. Strep-tag binds to the beads with an affinity much higher that of the biotin-streptavidin pair, thereby non-covalently attaching the sliding clamp protein/polypeptide (e.g. PCNA protein/polypeptide) to the carrier (in this case, Strep-Tactin® beads). For an antibody-antigen pair, the FLAG-epitope can be introduced to the sliding clamp protein/polypeptide (e.g. PCNA protein/polypeptide), while an anti-FLAG antibody can be attached to a carrier or surface to form FLAG beads, when the carrier is a bead or the surface forms part of a bead. Antibody binding to the antigen non-covalently conjugates the sliding clamp protein/polypeptide (e.g. PCNA protein/polypeptide) to the carrier. In general, the biotin group, streptavidin, avidin or NeutrAvidin, antibody, tag (e.g. strep-tag), and/or antigen can be attached to the sliding clamp protein/polypeptide (e.g. PCNA protein/polypeptide), and/or to the carrier or surface via any of the linkers described below, such as an unsubstituted alkylene linker or a polyether linker.

In the case of metal coordination, the sliding clamp protein/polypeptide (e.g. PCNA protein/polypeptide) can contain a group capable of coordinating with a metal associated with the bead, such as nickel (II) nitrilotriacetic acid (Ni-NTA) beads. For example, the group contains one or more aromatic groups (e.g. poly(histidine)) that chelate the metal (e.g. $Ni^{2+}$) thereby non-covalently conjugating the sliding clamp protein/polypeptide (e.g. PCNA protein/polypeptide) to the bead.

In the case of physical adsorption, a hydrophobic molecule, such as polymethacrylate or an alkyl group having at least about 10 carbons, may be attached to the sliding clamp protein/polypeptide (e.g. PCNA protein/polypeptide) or to the surface or carrier. The hydrophobic molecule will adsorb onto the surface of a hydrophobic surface or carrier, that contains molecules such as a polyorthoester, polysebacic anhydride, unmodified poly(lactic acid), or polycaprolactone, or moieties such as phenyl, butyl, or hexyl, thereby non-covalently conjugating the sliding clamp protein/polypeptide (e.g. PCNA protein/polypeptide) to the surface or carrier.

In some preferred embodiment, improved capturing of the SC by the carrier/support is accomplished employing two different types of affinity chemistry, for example, metal coordination and binding partner ligand complex formation. Thus, the sliding clamp is provided with two different affinity tags that can bind to their respective binding partners using different affinity chemistries. For example, the sliding clamp protein/polypeptide (e.g. PCNA protein/polypeptide) can contain a group capable of coordinating with a metal associated with the bead (first affinity chemistry), such as nickel (II) nitrilotriacetic acid (Ni-NTA) beads and a group capable of binding a ligand (for example biotin) (second affinity chemistry). This design improves capturing of SC by the carrier/surface used in the affinity purification system by removal of free unbound ligand (for example, biotin) by a first Ni-NTA (nitrilotriacetic acid). In some preferred embodiments, the sliding clamp protein is modified to contain a polyhistidine tag, for example, 4 to 10 histidine residues, preferably, 6 histidine residues and an AviTag (GLNDIFEAQKIEWHE (SEQ ID NO: 6). In this embodiment, the modified SC can bind to Ni-NT and the AviTag can bind to a biotin tag conjugated to the carrier/surface used to make the sliding clam-based affinity purification system. The sliding clamp is preferably engineered as a fusion protein containing at least two different types of affinity tags using methods shown in Example 4.

In this embodiment, the sliding clamp is engineered/modified for improved geometry and exposure of the tag (for example, biotin). For example, the tag modified sliding clamp protein can be further modified to place least one or preferably two flexible linkers between AviTag (GLN-DIFEAQKIEWHE (SEQ ID NO: 6) and the N-terminal of PCNA to better expose the AviTag and provide distance between PCNA from the carrier/support, for example agarose. The linkers can be introduced between the two tags and/or between the SC and the two tags. Exemplary linkers are Glycine-Serine linkers, for example, glycine-serine, (GGGGS) n (SEQ ID NO: 10), for example, GGGGS (SEQ ID NO: 9), GGGS (SEQ ID NO: 8), etc.

A particularly preferred sliding tag-based affinity column is the AviTag™-PCNA-Agarose column disclosed and exemplified herein (in Example 4).

III. Methods of Making and Reagents therefor

Methods of making the affinity system described herein generally involve covalent or non-covalent conjugation of a protein to a non-cellular surface, preferably, via a linker using an internal residue of the protein. Preferably, the conjugation involves the side chain of the internal residue. The internal residue can be a natural amino acid, a non-natural occurring amino acid, or a combination thereof. In the case of covalent conjugation, a preferred natural amino acid that can be used to mutate a residue of the protein is cysteine. In the case of non-covalent conjugation, pairs of systems that can be used include, but are not limited to, the affinity interactions described above (e.g. ligand-receptor complex formation: biotin and streptavidin, biotin and avidin or NeutrAvidin, Strep-tag and Strep-Tactin® pair, FLAG-epitope and anti-FLAG antibody), metal coordination: Ni-NTA and poly(histidine), and physical adsorption (e.g. hydrophobic interactions between polymethacrylate or an alkyl group having at least about 10 carbons, and polyorthoester, polysebacic anhydride, unmodified poly(lactic acid), or polycaprolactone, or moieties such as phenyl, butyl, or hexyl).

As a non-limiting example of how to generate an affinity system in which the protein is conjugated to surface (e.g. a non-cellular surface) via non-covalent linkage, a suitable expression vector can be introduced into a desired organism, such as *E. coli*, to express the protein. Several approaches can be used as exemplified herein with PCNA and AviTag. 1) co-expression of AviTag-sliding clamp (exemplidifed herein using PCNA) and BirA biotin-transferase enzyme in vivo in a desired organism, such as *E. coli*, from the same plasmid; 2) Co-transform in a desired organism, such as *E. coli*, two plasmids with different antibiotic resistance and different origin of replication: one containing AviTag-sliding clamp (exemplidifed herein using PCNA) and one containing BirA; 3) Purify AviTag-sliding clamp (exemplidifed herein using PCNA) alone and perform the biotinlyaltion reaction in vitro with purified BirA enzyme in specific buffer reactions that include free biotin; 4) Other systems of biotylation other than the AviTag/BirA system used either in vivo or in vitro.

In some forms, the plasmid contains one or more of the following:

(a) a gene at a first multiple cloning site (MCS), which codes for SEQ ID NO: 1, SEQ ID NO: 5, or a variant thereof containing between about 50% and about 100% sequence identity to SEQ ID NO: 1 or SEQ ID NO: 5, or at least 50%, 55%, 60%, 65%, 70%, 75%, 80%, 85%, 90%, 95%, 96%, 97%, 98%, 99% sequence identity to SEQ ID NO: 1 or SEQ ID NO: 5;

(b) a gene at the first MCS of the plasmid that codes for SEQ ID NO: 6, or a variant thereof containing between about 50% and about 100% sequence identity to SEQ ID NO: 6, or at least 50%, 55%, 60%, 65%, 70%, 75%, 80%, 85%, 90%, 95%, 96%, 97%, 98%, 99% sequence identity to SEQ ID NO: 6;

(c) a gene at the first MCS of the plasmid that codes for SEQ ID NO: 7, or SEQ ID NO: 8, or a variant thereof containing between about 50% and about 100% sequence identity to SEQ ID NO: 7 or SEQ ID NO: 8, or at least 50%, 55%, 60%, 65%, 70%, 75%, 80%, 85%, 90%, 95%, 96%, 97%, 98%, 99% sequence identity to SEQ ID NO: 7 or SEQ ID NO: 8. Preferably, the gene that codes for SEQ ID NO: 7, or SEQ ID NO: 8, or a variant thereof described herein, is inserted into the plasmid so that SEQ ID NO: 7, or SEQ ID NO: 8, or a variant thereof described herein, is co-expressed at the N-terminus of SEQ ID NO: 1, SEQ ID NO: 5, or a variant thereof described herein; or (d) a second MCS containing a gene that codes for an enzyme (e.g. a ligase). In some forms, the enzyme (e.g. ligase) is capable of transferring a molecule to SEQ ID NO: 6, or a variant thereof containing between about 50% and about 100% sequence identity to SEQ ID NO: 6, or at least 50%, 55%, 60%, 65%, 70%, 75%, 80%, 85%, 90%, 95%, 96%, 97%, 98%, 99% sequence identity to SEQ ID NO: 6. In some forms the enzyme (e.g. ligase) is a biotin ligase, and the molecule is biotin.

Non-limiting examples of combinations that can be selected from (a), (b), (c), and (d), include: (a) and (b); (a) and (c); (a) and (d); (a), (b), and (c); (a), (b), and (d), or (a), (b), (c), and (d). In some forms, such as when the plasmid contains (a), (b), (c), and (d), the plasmid can ensure the co-expression of (i) a protein containing SEQ ID NO: 1, SEQ ID NO: 5, or a variant thereof described herein, containing SEQ ID NO: 6, or a variant thereof described herein and SEQ ID NO: 7, or SEQ ID NO: 8, or a variant thereof described herein, at its N-terminal ready for biotinylation, and (ii) an enzyme (e.g. a ligase, such as a biotin ligase) that will transfer a molecule (e.g. biotin) covalently to the protein in (i).

If needed, the protein can then be purified from its medium (e.g. cell lysate) using suitable purification systems, such as an affinity column (e.g. a HisTrap™ affinity column). HisTrap™ HP is a ready to use column, prepacked with precharged Ni Sepharose™ High Performance which has high binding capacity and low nickel ion leakage that ensures reliable capture of target protein. Ni Sepharose High Performance (HP) affinity resists consists of highly cross-linked agarose beads to which a chelating group has been coupled. This chelating group is precharged with nickel, which selectively retains proteins with exposed histidine groups. Subsequently, the protein, preferably containing the transferred molecule (e.g. biotin), can be conjugated non-covalently to a surface (e.g. a non-cellular surface) containing a second molecule, such as avidin, stretavidin, NeutrAvidin, etc. which binds to biotin.

Further details on how to use this general approach to generate an affinity system that involves non-covalent conjugation of the protein to a non-cellular surface can be found in the Examples below.

Preferably, whether in a system that involves covalent or non-covalent linkage of the protein to a non-cellular surface, the protein is a recombinant protein expressed in a suitable organism, such as E. coli, using the genetic sequence from an organism that naturally expresses the protein or via in silico codon optimization approaches. Therefore, a genetic sequence coding for the protein of interest can be obtained from an organism that naturally expresses the protein. Typically, the protein or the genetic sequence coding for the protein is from eukaryotes, archaea, bacteria, viruses, or a combination thereof. Exemplary species from which the genetic sequence coding the protein can be isolated include: *Homo sapiens, Macaca fascicularis, Macaca nemestrina, Rhinopithecus bieti, Gorilla gorilla gorilla, Nomascus, leucogenys, Mandrillus leucophaeus, Neovison vison, Ovis aries, Bos taurus, Rattus norvegicus, Oryza sativa, Mus musculus, Saccharomyces cerevisiae, Saccharolobus solfataricus, Pyrococcus furiosus, Archaeoglobus fulgibus, Thermococcus kodakarensis, Leishmania donovani, Sulfurisphaera tokodaii*, Murine leukemia virus, *Haloferax volcanii, Penaeus vannamei, Ricinus communis, Thermococcus gammatolerans*, or a combination thereof. In some forms, the genetic sequence coding the protein is from a *Homo sapiens*. Preferably, the protein is a PCNA.

Preferably, the genetic sequence is introduced into the organism via a vector. Nucleic acids in vectors can be operably linked to one or more expression control sequences. For example, the control sequence can be incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, lentiviruses and adeno-associated viruses. Numerous vectors and expression systems are commercially available from such corporations as Novagen (Madison, WI), Clontech (Palo Alto, CA), Stratagene (La Jolla, CA), and Invitrogen Life Technologies (Carlsbad, CA).

Methods of making and using vectors for in vivo insertion of nucleic acids are known in the art.

For example, the delivery vehicle can be a viral vector, for example a commercially available preparation, such as an adenovirus vector (Quantum Biotechnologies, Inc. (Laval, Quebec, Canada). The viral vector delivery can be via a viral system, such as a retroviral vector system which can package a recombinant retroviral genome. The recombinant retrovirus can then be used to infect and thereby deliver to the infected cells nucleic acid encoding a protein of interest. The exact method of introducing the altered nucleic acid into the host cell is, of course, not limited to the use of retroviral vectors. Other techniques are widely available for this procedure including the use of adenoviral vectors, adeno-associated viral (AAV) vectors, lentiviral vectors, pseudo-typed retroviral vectors, and others described in (Soofiyani, et al., *Advanced Pharmaceutical Bulletin*, 3 (2): 249-255 (2013). Viruses can be modified to enhance safety, increase specific uptake, and improve efficiency (see, for example, Zhang, et al., *Chinese J Cancer Res.*, 30 (3): 182-8 (2011), Miller, et al., FASEB J, 9 (2): 190-9 (1995), Verma, et al., *Annu Rev Biochem.*, 74:711-38 (2005)).

Physical transduction techniques can also be used, such as liposome delivery and receptor-mediated and other endocytosis mechanisms (see, for example, Schwartzenberger et al., *Blood*, 87:472-478 (1996)). Commercially available liposome preparations such as LIPOFECTIN, LIPO-FECTAMINE (GIBCO-BRL, Inc., Gaithersburg, Md.), SUPERFECT (Qiagen, Inc. Hilden, Germany) and TRANS-FECTAM (Promega Biotec, Inc., Madison, Wis.), as well as other liposomes developed according to procedures standard in the art are well known. In addition, nucleic acid or vectors encoding proteins of interest can be delivered in vivo by electroporation as well as by means of a sonoporation. During electroporation electric pulses are applied across the cell membrane to create a transmembrane potential difference, allowing transient membrane permeation and transfection of nucleic acids through the destabilized membrane (Soofiyani, et al., *Advanced Pharmaceutical* Bulletin, 3 (2): 249-255 (2013)). Sonoporation combines the local application of ultrasound waves and the intravascular or intratissue administration of gas microbubbles to transiently increase the permeability of vessels and tissues (Escoffre, et al., *Curr Gene Ther.*, 13 (1): 2-14 (2013)). Electroporation and ultrasound based techniques are targeted transfection methods because the electric pulse or ultrasound waves can be focused on a target tissue or organ and hence gene delivery and expression should be limited to thereto. Expression or overexpression of the disclosed proteins can be accomplished with any of these or other commonly used gene transfer methods, including, but not limited to hydrodynamic injection, use of a gene gun.

Alternatively, the genetic sequence can be stably inserted into the genome of the organism expressing the protein. In some form, the internal residue is introduced into the protein via site-directed mutagenesis. Accordingly, in some forms, the genetic sequence coding for the protein of interest is mutated to insert specified nucleotides within the plasmid vector, to form codons that code for the internal residue used for conjugation. Protocols for performing site-directed mutagenesis and protein expression are known in the art. Kumar, et al., *Proc. Natl. Acad. Sci.* 2010, 107 (107), 19736-19741 and Hallak, et al., *PLOS ONE* 12 (6): e0177788 describe site-directed mutagenesis and/or protein expression methods, the contents of which are incorporated herein by reference. Preferably, the mutations do not degrade the structural stability or functional properties of the gene product (e.g. the protein).

In some forms, after the protein has been mutated to include the internal residue used for conjugation, the side chain of the internal residue can be further chemically modified to include a reactive group. Exemplary reactive groups include, but are not limited to, thiol, alkyne, azide, amine, hydroxy, hydrazide, ketone, sulfonyl chloride, aromatic diazonium, anilines or phenols, dialkyl dialkoxysilane, diaryl dialkoxysilane, cyano, isocyano, phosphonate, trityl chloride, and vinyl ether. The reactive group is capable of reacting with another chemical group attached (preferably through a linker) to the non-cellular surface via chemical synthesis strategies.

The Example below provides a preferred method of making the affinity system described herein. In one embodiment, a sample containing an engineered/modified SC, for example a cell lysate containing a SC fusion protein exemplified herein with biotinylated AviTag™-His-PCNA) is applied to an affinity column designed to bind proteins with exposed histidine groups, for example, the HisTrap™ affinity column, that has been pre-equilibrated with Buffer A. The engineered/modified SC is eluted using an appropriate buffer as exemplified herein with Buffer B. The eluted SC fusion can be used for coupling immediately or stored at −80° C. for later use or shipping purposes. This PCNA-coupled resin is then packed into a column, and washed with Buffer C to to release any non-specifically-bound PCNA.

The SC fusion eluted from the HisTrap column is subsequently incubated with a carrier modified to contain biotin binding partner, for example NeutrAvidin™ Agarose Resin under conditions that allow binding of the biotin to its binding partner (for example, for 2 hours at 4° C.). An appropriate buffer exemplified herein by Buffer C is then added to the resin to produce a slurry. The removal of the free unbound biotin by a first Ni— NTA (nitrilotriacetic acid) step yields almost complete capturing of the fusions by the avidin resin.

A preferred sliding tag-based affinity column is the Avi-Tag™-PCNA-Agarose column disclosed and exemplified herein (in Example 4).

IV. Methods of Using

The affinity system can be used to select a target molecule from a sample containing the target molecule. Preferably, the protein containing the bait function, which is conjugated to the surface or carrier is expressed in a wide range of organisms and is, optionally, a binding partner to several enzymes and non-enzymatic proteins (referred to herein, as a target protein). Therefore, the affinity system can be used to isolate several target proteins.

Preferably, the affinity system can be incorporated into a column to form a sliding clamp-based affinity column, and the column used as an affinity column for the purification of target proteins involved in, but not limited, to DNA replication and/or repair, cellular signaling and a combination thereof. This disclosed sliding clamp-based affinity system can be used to purify proetins proteins directly from crude extracts.

As shown in the Examples, this column can be used to purify target proteins in one chromatographic step. However, if needed, further chromatographic steps, such as such as affinity, ion exchange, size exclusion, or hydrophobic adsorption, can be added to the purification process. The method includes introducing a sample containing protein to be purified (target protein sample) into the disclosed affinity system, and eluting protein bound to the sliding clamp protein using an appropriate buffer. In some embodiments, the sample is a cell lysate, for example, a crude cell lysate. In some preferred embodiments, the method does not include any cofactors added to the target protein sample, for example a cell lysate sample.

A soluble fraction of the cell lysate containing the target protein is applied to the sliding clamp-based column that has pre-equilibrated with a buffer. Buffer D, is exemplified herein in embodiments where the column is a PCNA-agarose column employing a non-covalent coupling of the PCNA to agarose, as disclosed herein. The column was then washed with the same Buffer D or it may be washed with a different equivalent buffer. The target protein is eluted from the column with a linear gradient of a buffer, for example, Buffer E, in embodiments where the column is a PCNA-agarose column. buffer D [50 mM Tris-HCl (pH 7.5), 80 mM NaCl, 10 mM β-Mercaptoethanol and 5% Glycerol] and buffer E [50 mM Tris-HCl (pH 7.5), 1000 mM NaCl, 10 mM β-Mercaptoethanol and 5% Glycerol].

Combinations of buffers can be used in different purification steps in embodiments where the PCNA is directly coupled to the carrier, for example agarose bead via covalent coupling are provided in Table 1 for different purification steps. In some forms, the target proteins are proteins that naturally interact with the sliding clamp proteins/polypeptides (e.g. PCNA protein/polypeptide) in the disclosed affinity system. Some examples of these target proteins that can be purified using the disclosed sliding clamp, for example, PCNA protein/polypeptide-based affinity system include, but are not limited to, Ligase 1, Flap Endonuclease 1 (FEN 1), DNA polymerase Kappa, DNA polymerase Iota, DNA polymerase Eta, DNA polymerase Delta, and p15. A column containing the affinity system containing PCNA protein/polypeptide can be used to purify a broad range of proteins, given that DNA clamps are present in all species, PCNA protein/polypeptide can be easily replaced by the DNA clamp of an organism of interest, to purify the interacting proteins from that organism.

In some forms, the target proteins are proteins that do not naturally interact with sliding clamp proteins/polypeptides (e.g. PCNA protein/polypeptide). In these forms, such target proteins are modified to include sliding clamp protein/polypeptide (e.g. PCNA protein/polypeptide)-interacting peptides, such as by genetically engineering a cell to express the target protein containing a sliding clamp, (for example PCNA) interaction peptide. There is a constant demand for affinity tags for protein purification. Most of these tags are either relatively large in size (for example GST or MBP) or rely on antibody-based columns (for example HA tag). Among the small (<20 amino acids) tags His and Strep tags are very popular choices. In a preferred embodiment, the tag is a small tag.

Prior to engineering, the cell can be a stem cell, a progenitor cell, or a terminally differentiated cell. Suitable sources from which cells can be obtained and engineered include, but are not limited to, *Homo sapiens, Macaca fascicularis, Macaca nemestrina, Rhinopithecus bieti, Gorilla gorilla gorilla, Nomascus, leucogenys, Mandrillus leucophaeus, Neovison vison, Ovis aries, Bos taurus, Rattus norvegicus, Oryza sativa, Mus musculus, Saccharomyces cerevisiae, Saccharolobus solfataricus, Pyrococcus furiosus, Archaeoglobus fulgibus, Thermococcus kodakarensis, Leishmania donovani, Sulfurisphaera tokodaii, Murine leukemia* virus, *Haloferax volcanii, Penaeus vannamei, Ricinus communis, Thermococcus gammatolerans, E. coli* or a combination thereof. Many proteins interact with sliding clamp protein/polypeptide (e.g. PCNA protein/polypeptide) via two known PCNA-interacting motifs PCNA-interacting peptide (PIP) box (Warbrick, Bioessays 1998, 20 (3), 195-199) and AlkB homologue 2 PCNA interacting motif (APIM) (Mailand, et al., Nature Reviews: Molecular Cell Biology 2013, 14 (5), 269-282). As an example, the PIP box peptide sequence can be GRKRRQTSMTDFYHSKRRLIFS (SEQ ID NO: 4) of human p21. The contents Warbrick, *Bioessays* 1998, 20 (3), 195-199 and Mailand, et al., Nature Reviews: *Molecular Cell Biology* 2013, 14 (5), 269-282 are hereby incorporated by reference. The Examples demonstrate introduction of a tag derived from the PIP box of human p21 as an alternative or complement to the current affinity tags. This tag is small in size and extends the usage of PCNA-based column to affinity purifications of proteins that do not naturally bind to PCNA. Through its small size and its strength of interaction with PCNA this tag is a preferred tag for protein purification using PCNA as bait for non-PCNA binding protein. The studies in this application show for the first time that this peptide can be used as a tag for affinity purification of fusion proteins that contain it and experimentally prove that the tag is available for binding, resulting in very high purity of the target protein.

In addition, peptide sequences that interact with sliding clamp protein/polypeptide can be derived from the conserved peptide linear motifs in DNA polymerases. Examples are described in Dalrymple, et al., Proc. Natl. Acad. Sci. 2001, 98 (20), 11627-11632, the contents of which are hereby incorporated by reference. Some examples of conserved linear motifs have the consensus sequence QxxLxxFF, where x is any amino acid, or QLxLF where x is an amino acid with a small side chain (Dalrymple, et al., *Proc. Natl. Acad. Sci.* 2001, 98 (20), 11627-11632). Examples of amino acids with small side chains include, but are not limited to, glycine, alanine, cysteine, serine, threonine, aspartate, and asparagine. In some forms, these target proteins can also be modified to include full-length sliding clamp (e.g. PCNA protein/polypeptide)-interacting proteins. Examples of full-length sliding camp-interacting proteins include, but are not limited to, those described above: ligase 1, Flap Endonuclease 1 (FEN 1), DNA polymerase Kappa, DNA polymerase Iota, DNA polymerase Eta, DNA polymerase Delta, and p15.

Further, the column can be used in high-throughput screening for therapeutic peptides that bind to DNA clamps with the purpose of blocking clamp-protein interactions involved in DNA Replication or Repair of over-replicating cells, such as cancer cells. Proliferating cell nuclear antigen (PCNA) plays an essential role in regulating DNA synthesis and repair and is indispensable to cancer cell growth and survival. Previously a novel cancer associated PCNA isoform (dubbed caPCNA), which was ubiquitously expressed in a broad range of cancer cells and tumor tissues, but not significantly in non-malignant cells was reported.

The ease of generating the affinity system shows that a column containing the affinity system can be readily produced, by scaling up the production of proteins (e.g. PCNA or alternative clamps).

The methods, compounds, and compositions herein described are further illustrated in the following examples, which are provided by way of illustration and are not intended to be limiting. It will be appreciated that variations in proportions and alternatives in elements of the components shown will be apparent to those skilled in the art and are within the scope of disclosed forms. Theoretical aspects are presented with the understanding that Applicants do not seek to be bound by the theory presented. All parts or amounts, unless otherwise specified, are by weight.

EXAMPLES

As a proof of concept, PCNA was used to purify various PCNA-binding proteins that are involved in the maturation of Okazaki fragments during lagging strand synthesis, translesion DNA synthesis, and genome stability. On the lagging strand, DNA primase-polymerase alpha (Polα) synthesizes a hybrid RNA-DNA primer to initiate Okazaki fragment synthesis. Replication factor C(RFC) opens the PCNA clamp and loads it onto the primer-template junction. DNA polymerase delta (Polδ) binds PCNA and extends the Okazaki fragment with high processivity. When Polδcollides with the previously synthesized Okazaki fragment, it displaces the RNA primer, generating a flap structure. Flap endonuclease 1 (FEN1) cleaves the flap and leaves behind a nick that is sealed by DNA Ligase 1 (Lig1). PCNA orchestrates the activities of Polδ, FEN1, and Lig1 through its interactions with their PIP motifs (Gomes and Burgers, Embo Journal 2000, 19, 3811-3821; Dovrat, et al., *Proc. Natl. Acad. Sci. USA* 2014, 111, 14118-14123).

Example 1: Protein Affinity Columns with PCNA-Binding Proteins

In this work, human Proliferating Cell Nuclear Antigen (PCNA) was used as a bait in a purification protocol to purify interacting proteins. PCNA is dsDNA clamp that acts as a processivity factor for DNA polymerase 8 in eukaryotic cells. It plays a key role in replication and also acts as a binding partner for multiple other factors (over 200 proteins). PCNA is a homo-trimeric ring-shaped protein composed of 261 amino-acids and a molecular mass of 29 kDa for each domain. DNA clamps, such as PCNA, are evolutionarily well-conserved protein found in wide variety of diverse organisms including animals, yeast and higher plants as well as in Archaea. Sequence, structure and function conservation among various species and the large number of proteins they interact with make DNA clamps suitable baits to purify interacting partners.

Human PCNA was efficiently coupled to agarose resin via sulfhydryl-iodoacetic chemistry to form a stable thioether bond. The sulfhydryl group is provided by an exogenous cysteine, replacing asparagine 107 (N107) (FIG. 1A). This mutation does not affect PCNA stability and its loading on DNA (Hedglin, et al., *Elife* 2013, 2; Hedglin, et al., *Biochemistry* 2017, 56, 3415-3421). At different purification steps this column was used for seven proteins involved in DNA Replication (Polδ, FEN1, and Lig1), TLS (Polη, Polκ, and Polι) and genome stability (p15). Moreover, the application of the PCNA-Agarose column was extended to purify proteins that do not bind PCNA, by fusing a peptide tag coding for the PIP motif of human p21 to the protein of interest. Finally, methods for analyzing the elution profiles of the purified proteins have been provided, and it is concluded that the PCNA-Agarose column is a useful analytical tool for characterizing the relative strength of the interaction of PCNA with its binding proteins.

Materials and Methods

Using site-directed mutagenesis, surface exposed asparagine (N) 107 of PCNA, which was previously used for labelling studies (Hedglin, et al., *Biochemistry*, 56:3415-3421 (2017)), was mutated to cysteine (C). Thermo Scientific SulfoLink® Coupling Resin was used for covalent immobilization of sulfhydryl-containing proteins. Thermo Scientific SulfoLink® Coupling Resin is porous, cross-linked, 6% beaded agarose that has been activated with iodoacetyl groups for covalent immobilization of cysteine-peptides and other sulfhydryl molecules. Features of Sulfo-Link Coupling Resin: specific to sulfhydryl (—SH) groups—iodoacetyl groups react specifically with sulfhydryls to form irreversible thioether bonds; flexible coupling conditions—can use pH 7.5 to 9.0 aqueous buffers, organic solvent (e.g., 20% DMSO) or denaturant (guanidine. HCl), as needed for protein or peptide solubility during coupling reaction When incubated with a solution of protein that contains reduced cysteine residues, the iodoacetyl groups of Sulfo-Link® Coupling Resin reacts selectively and efficiently with the exposed sulfhydryl (—SH) group of cysteine to form a stable, irreversible covalent thioether bond that permanently attaches the protein to the resin. This resulted in a custommade affinity resin for purification of interacting partners. A schematic showing the attachment of PCNA to the resin is shown in FIG. 1A.

Site-directed mutagenesis provides the advantage by the fact that the site where the exogenous cysteine is introduced and where the coupling takes place was precisely controlled. This strategy ensures that both faces of PCNA are accessible to provide native binding conditions at full capacity. The column was produced using the PCNA attached resin, and used to purify seven different proteins.

5 μL of each fraction analyzed on each gel was mixed with 10 μL standard loading dye. The gel was run for 45 minutes in MOPS based running buffer. The gels were stained with Coomassie Blue and detained in water and imaged using BioRad Gel Imager.

i. Plasmid Construction

Oligonucleotides for all genes were synthesized by Integrated DNA Technologies (IDT) (Heverlee, Belgium). *Escherichia coli* (*E. coli*) codon optimized expression plasmids were constructed as follows. Human Polη (accession no. NP006493), Polκ (accession no. NP057302), Polι (accession no. NP009126), FEN1 (accession no. 004102), Lig1 (accession no. NP000225), p15 (accession no. NP055551), *E. coli* replication termination protein Tus (accession no. BAJ43409) and PCNA (accession no. NP002583) were synthesized from IDT. Full-length sequences of Polη, Polκ, Polι, Tus, and p15 were amplified by PCR and cloned into pESUMO pro Kan+(LifeSensors) to obtain N-terminally Histidine- and SUMO-tagged proteins using the Gibson cloning protocol (Gibson, et al., Nature Methods 2009, 6, 343-U341; Gibson, et al., Nature Methods 2010, 7, 901-U905), which was successfully used before (Iwata, et al., Nucleic Acids Res. 2013, 41, 9129-9140; Rashid, et al., Elife 2017, 6; Rashid, et al., Nat. Commun. 2019, 10, 2104). The PIP motif sequence of p21 was also added before the Histidine tag in Tus in the pESUMO pro Kan+plasmid by PCR (construct named hereafter PIP$^{p21}$-Tus). FEN1 and Lig1 were cloned in pRSF-1b Kan$^+$(Novagen) using Gibson cloning protocol. PCNA was cloned into pETDuet-1 MCS1 Amp+ (Novagen) to obtain N-terminally Histidine-tagged protein using the Gibson cloning protocol (hereafter named as PCNA). After cloning PCNA, asparagine 107 to cysteine (N107C) mutation was carried out using the Quick-change Site-Directed Mutagenesis Kit (Stratagene). Strep- and Flag-tags were added before His-tag in PCNA plasmid by PCR (hereafter named as Strep-PCNA and Flag-PCNA, respectively).

The MultiBac expression system (Bieniossek, et al., Curr. Protoc. Protein Sci. 2008, Chapter 5, Unit 5 20) was used to express human Polδ in Sf9 insect cells. Briefly, p125 (accession no. NP002682) and p50 (accession no. NP006221) were amplified and cloned into pACEBac1 Gent$^+$at BamHI and XbaI restriction sites separately. The p50 cassette along with the promoter and terminator were excised with I-Ceul and BstX1 and ligated into p125 containing pACEBac1 linearized with I-Ceul. The p68 (accession no. NP006582) was amplified and cloned into pIDC Cm$^+$at BamHI and XbaI restriction sites. The p12 (accession no. NP066996) was amplified along with 12 Histidine residues at the N-terminus and cloned into pIDS Spect$^+$at XhoI and NheI restriction sites. Finally, the single transfer vector with different subunit assemblies was generated using cre recombinase according to the MultiBac expression system user manual. In the last step, the recombinant transfer vector containing the gene expression cassettes of all four subunits was introduced into MultiBac baculoviral DNA in DH10MultiBac and bacmid DNA was isolated.

ii. Expression of Recombinant Proteins

*E. coli* strain BL21 (DE3) (Novagen) was used for the expression of all recombinant proteins except for Polδ which was expressed in Sf9 cells. Briefly, Polη, Polκ, Polι, Lig1, and p15 were transformed in BL21 (DE3) cells and grown in 2YT media supplemented with the kanamycin at 24° C. to an $OD_{600}$ of 0.8, followed by induction with 0.1 mM isopropyl β-D-thiogalactopyranoside (IPTG) for 19 hrs at 16° C. FEN1, PIPP21-Tus, and PCNA were transformed in BL21 (DE3) cells and grown in 2YT media supplemented with the appropriate antibiotics at 37° C. to an $OD_{600}$ of 0.8 for FEN1 and PIPP21-Tus, and an $OD_{600}$ of 1.25 for PCNA. Expression was then induced with 0.5 mM IPTG for 19 hrs at 16° C. The cells were harvested by centrifugation at 5,500×g for 10 min, and the resulting pellets were re-suspended in 3 ml per 1 g of wet cells in lysis buffer [50 mM Tris-HCl pH (7.5), 750 mM NaCl, 5 mM β-Mercaptoethanol, 0.2% NP-40, 1 mM PMSF, 5% Glycerol and EDTA free protease inhibitor cocktail tablet/50 ml (Roche, UK)]; the lysis buffer in the case of FEN1, Lig1, and p15 contains 80 mM NaCl instead of 750 mM, and in the case of PIPP21-Tus the pH of was 8.0 instead of 7.5.

For Polδ, Sf9 cells were cultured in ESF 921 medium (Expression Systems). Briefly, bacmid DNA containing all four subunits was transfected to Sf9 cells using FuGENE HD (Promega) according to the manufacturer's instructions. The resulting supernatant was obtained as the P1 virus stock, which was then amplified to obtain the P2 virus stock. Next, the P2 virus stock was amplified to obtain the P3 virus stock for large scale expression. For expression of Polδ, 2 L of suspension culture of Sf9 cells at $2\times10^6$ cells/ml was infected with the P3 virus stock for 72 hrs. Cells were harvested by centrifugation at 5,500×g for 10 min and then re-suspended in 3 ml per 1 g of wet cells in lysis buffer [50 mM Tris-HCl pH (7.5), 500 mM NaCl, 5 mM β-Mercapto-ethanol, 1 mM PMSF, 5% Glycerol and EDTA free protease inhibitor cocktail tablet/50 ml].

Cell pellets of all protein-expression cultures were lysed using 2 mg/ml lysozyme at 4° C. for 30 min followed by sonication. Cell debris was removed by centrifugation at 22,040×g for 1 hr at 4° C. In case of Polδ, cells were lysed only by sonication and debris was removed by centrifugation at 95,834×g for 1 hr at 4° C.

iii. Chromatography Columns and Resins

His Trap HP 5 mL (hereafter named HisTrap), HiLoad 16/600 Superdex 200 pg (hereafter named gel filtration 200 pg), HiLoad 16/600 Superdex 75 pg (hereafter named gel filtration 75 pg), HisTrap Blue 1 mL (hereafter named HiTrap Blue) were purchased from GE Healthcare. AP-1 column was purchased from Waters Corporation. SulfoLink Coupling resin (hereafter named SulfoLink resin) was purchased from Thermo Fisher scientific.

iv. Estimating the Efficiency of PCNA-Coupling to Various Resins

PCNA, Flag-PCNA and Strep-PCNA were all purified as described below for PCNA N107C. The coupling of PCNA to SulfoLink resin was performed under reducing condition as described below for PCNA N107C. Flag-PCNA was bound to Anti-Flag M2 affinity gel (Sigma), while Strep-PCNA was bound to Strep-Tactin superflow plus (Qiagen) by following the manufacturer's instructions. The coupling of PCNA to NHS-activated dry agarose resin (Pierce) was performed by following the manufacturer's instructions with an extreme care to the pH adjustment.

For all coupling schemes, a 3 ml fraction of ~8 mg/ml PCNA was used. This fraction was mixed with 1 ml of pre-equilibrated resin of interest in accordance with the manufacturer's instructions except for increasing the incubation time to 12 hrs at 4° C. Following this incubation, the resin was spun down and the percentage of protein in the flow-through was quantified by measuring the absorbance at 280 nm. Extinction coefficient of PCNA homo-trimer is 47790 M-1 cm-1. The resin was washed for 20 min with washing buffer as per manufacturer's instructions and the percentage of protein in the wash was quantified by measuring the absorbance at 280 nm. The percentage of bound PCNA was estimated by subtracting the sum of the percentages in the flow-through and the wash from the total amount. Each measurement was performed in triplicate. The mean and standard deviation of the three measurements are reported, along with the individual points as bar charts.

Results i. Purification and Conjugation of PCNA with SulfoLink Resin and Comparison With Other Resins Supernatant of PCNA N107C was mixed with 20 mM imidazole and directly loaded onto a HisTrap column equilibrated with buffer 1 (Table 1).

TABLE 1

Buffers and their composition used in different purification steps.

| Buffer No. | Composition |
|---|---|
| 1 | 50 mM Tris-HCl (pH 7.5), 500 mM NaCl, 20 mM Imidazole, 5 mM β-Mercaptoethanol and 5% Glycerol. |
| 2 | 50 mM Tris-HCl (pH 7.5), 500 mM NaCl, 500 mM Imidazole, 5 mM β-Mercaptoethanol and 5% Glycerol. |
| 3 | 50 mM Tris-HCl (pH 7.5), 150 mM NaCl and 0.5 mM TCEP. |
| 4 | 50 mM Tris-HCl (pH 7.5), 750 mM NaCl and 50 mM DTT. |
| 5 | 50 mM Tris-HCl (pH 7.5), 500 mM NaCl, 40 mM Imidazole, 5 mM β-Mercaptoethanol and 5% Glycerol. |
| 6 | 50 mM Tris-HCl (pH 7.5), 80 mM NaCl, 40 mM Imidazole, 5 mM β-Mercaptoethanol and 5% Glycerol. |
| 7 | 50 mM Tris-HCl (pH 7.5), 80 mM NaCl, 500 mM Imidazole, 5 mM β-Mercaptoethanol and 5% Glycerol. |
| 8 | 50 mM Tris-HCl (pH 7.5), 80 mM NaCl, 5 mM β-Mercaptoethanol and 5% Glycerol. |
| 9 | 50 mM Tris-HCl (pH 7.5), 1.5 M NaCl, 5 mM β-Mercaptoethanol and 5% Glycerol. |
| 10 | 50 mM Tris-HCl (pH 7.5), 500 mM NaCl, 5 mM β-Mercaptoethanol and 5% Glycerol. |
| 11 | 50 mM Tris-HCl (pH 8.0), 500 mM NaCl, 30 mM Imidazole, 10 mM β-Mercaptoethanol, and 5% Glycerol. |
| 12 | 50 mM Tris-HCl (pH 8.0), 160 mM NaCl, 30 mM Imidazole, 10 mM β-Mercaptoethanol, and 5% Glycerol. |
| 13 | 50 mM Tris-HCl (pH 8.0), 160 mM NaCl, 500 mM Imidazole, 10 mM β-Mercaptoethanol and 5% Glycerol. |
| 14 | 50 mM Tris-HCl (pH 8.0), 80 mM NaCl, 10 mM β-Mercaptoethanol and 5% Glycerol. |
| 15 | 50 mM Tris-HCl (pH 8.0), 250 mM NaCl, 20 mM imidazole, 10 mM β-Mercaptoethanol, and 5% Glycerol. |

The column was washed with 50 ml of buffer 1 and the bound PCNA was eluted using 50 ml gradient with buffer 2 (Table 1). Eluents were concentrated to 1.5 ml and then incubated with 20 mM DTT for 15 min at 4° C. on a shaker to reduce the sulfhydryl groups of the cysteine residues on PCNA (FIG. 1A). The reduced PCNA was then loaded onto a gel filtration 200 pg pre-equilibrated with buffer 3 (Table 1). The eluents were concentrated to 3 ml at a final concentration of 20 mg/ml and mixed with 3 ml of SulfoLink resin pre-equilibrated with buffer 3 (Table 1). The complex was gently flushed with gaseous nitrogen to prevent oxidation, and the lid was closed instantly. The tube was covered with aluminum foil and kept at room temperature (RT) for 1 hr followed by overnight incubation at 4° C. on a shaker. Next, the supernatant was decanted, and the PCNA-coupled resin was washed twice with buffer 4 (Table 1) to remove the excess PCNA and to block the resin. Finally, the resin was packed in an AP-1 column for subsequent purification steps. Hereafter, this column will be referred to as the PCNA-Agarose column.

Next, this column was compared in terms of efficiency of PCNA coupling to the resin with several covalent and noncovalent coupling schemes (FIG. 1B). Introducing the mutation N107C on PCNA increases the efficiency of coupling from ~30% to ~85%. The SulfoLink coupling scheme exhibited the highest percentage of captured PCNA. Strep-PCNA linked to Strep-Tactin superflow plus also exhibited a relatively high efficiency of binding. However, the non-covalent coupling in Strep-PCNA is unpreferable since PCNA can be depleted over the extended periods required for protein loading, washing and elution. NHS coupling of PCNA via its N-terminal amine group to NHS-activated dry agarose resin resulted in an average coupling efficiency of ~65%. Out of all schemes, Flag-PCNA coupling to Anti-Flag M2 affinity gel resulted in the lowest percentage of bound protein, rendering this scheme undesirable for protein-coupled resins.

ii. Purification of Human Polδ

Figure 6A:
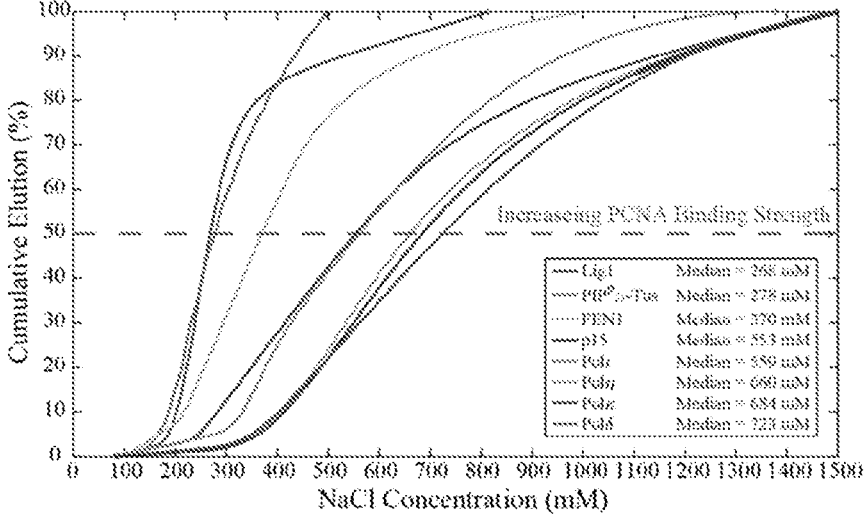
FIGS. 6A and 6B show analyses of the elution chromatograms of the purified proteins from the PCNA-Agarose column.
Figure 6B:
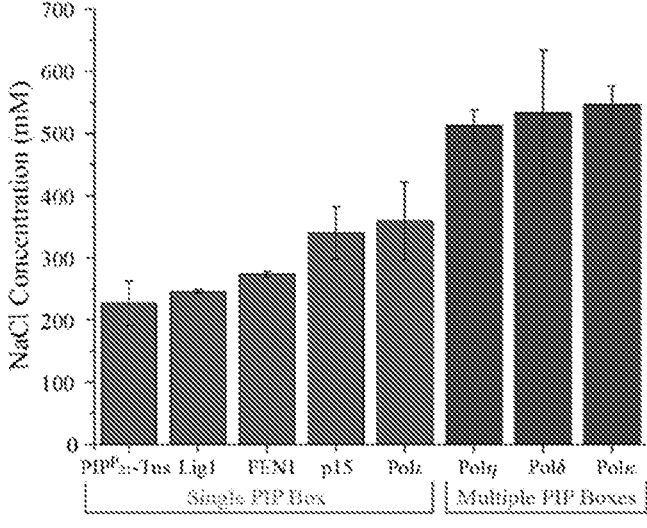
Figure 7A:
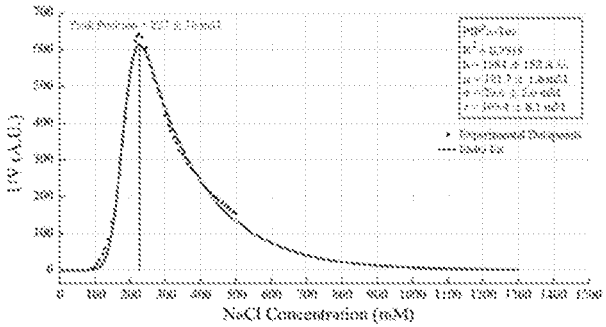
Figure 7B:
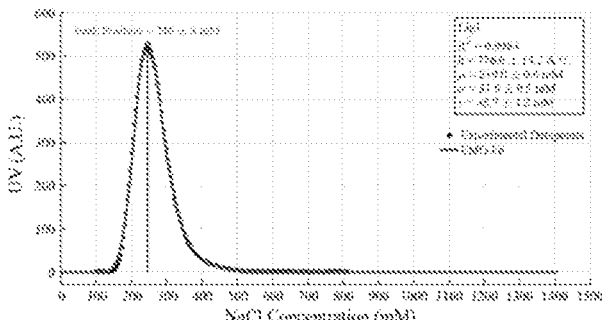
Figure 7C:
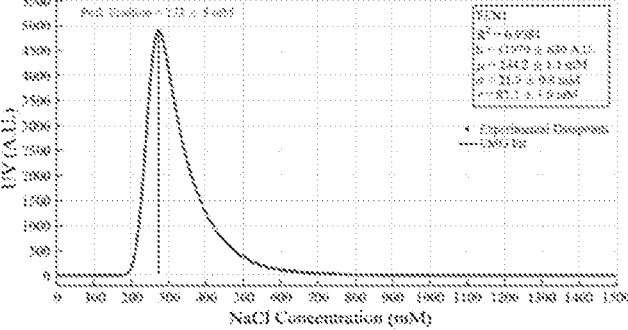
Figure 7D:
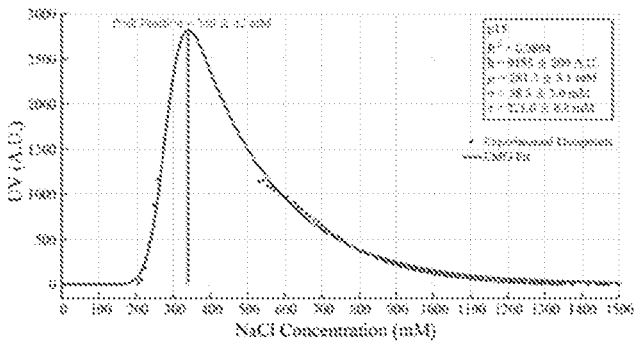
Figure 7E:
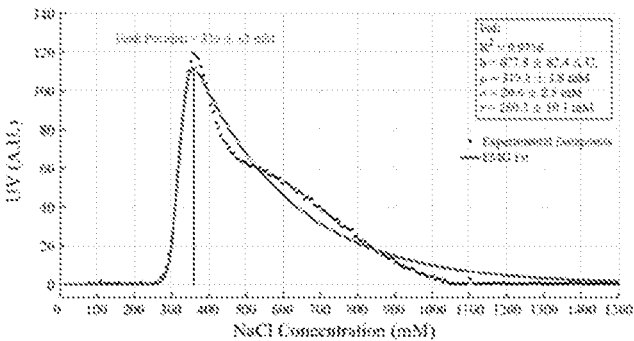

Here, the ability of the PCNA-Agarose column to purify a multi-subunit protein complex was tested. The supernatant from the cell pellets was mixed with 40 mM imidazole and directly loaded onto a HisTrap column equilibrated with buffer 5 (Table 1). The unbound proteins were washed with 50 ml of buffer 5, followed by washing with 50 ml of buffer 6 (Table 1) to reduce the salt concentration. The bound proteins were eluted with 50 ml gradient of buffer 7 (Table 1) (FIG. 2B, Lane 3). The fractions that contained all Polδ subunits were combined and loaded onto the PCNA-Agarose column pre-equilibrated with buffer 8 (Table 1) at a flow rate of 1 ml/min. The unbound proteins were removed by washing with 50 ml of buffer 8. Polδ was eluted with 50 ml gradient, from 80 mM to 1.5 M NaCl (Buffer 9, Table 1) (FIG. 2B, Lane 5). The intact Polδ complex was successfully separated from other heterogeneous complexes and impurities and eluted at ~534 mM of NaCl (FIGS. 6A, 6B, and 7G, and Table 2).

directly loaded onto the PCNA-Agarose column pre-equilibrated with buffer 8 (Table 1) at a flow rate of 1 ml/min. After washing, bound proteins were eluted with a gradient from 80 mM to 1.5 M NaCl (Buffer 9, Table 1). Nearly 80% purity of FEN1 (FIG. 3B, lane 3), Lig 1 (FIG. 3D, Lane 3) and p15 (FIG. 3F, Lane 3) was achieved demonstrating the high specificity of the column. Both FEN1 and Lig1 were eluted at ~273 and ~246 mM NaCl, respectively (FIGS. 6A, 6B, 7B and 7C, and Table 2), while p15 was eluted at ~340 mM NaCl (FIGS. 6A, 6B, and 7D, and Table 2). In the second step, FEN1 was loaded onto a gel filtration 75 pg, and ligase was loaded onto a HiTrap Blue column to remove the remaining impurities (FIG. 3B, Lane 4 and FIG. 3D, Lane 5). Since p15 also has His- and SUMO-tag, the remaining impurities were removed using a Histrap column. In this step, p15 eluents were mixed with 40 mM imidazole, loaded onto the column and then eluted with 15 ml gradient from 40 mM to 500 mM imidazole (FIG. 3F, Lane 5). The p15 eluents were then dialyzed overnight in buffer 10 (Table 1) and treated with SUMO protease to remove the SUMO tag and generate the native p15. Finally, the dialyzed protein was passed again through a HisTrap column, and the untagged protein was collected in the flow-through fractions (FIG. 3F, Lane 7).

iv. Purification of TLS DNA Polymerases (Polκ, Polι, Polη)

In this section, the effectiveness of the PCNA-Agarose column for various steps in the purification process was examined. The supernatants from the cell pellets of Polκ, Polι, Polη were prepared as described above for PCNA and then mixed with 40 mM imidazole. The supernatants for Polk and Poli were loaded directly onto a HisTrap column pre-equilibrated with buffer 5 (Table 1). The unbound proteins were washed with 50 ml of buffer 5 followed by washing with 50 ml of buffer 6 (Table 1) to reduce the salt concentration. The bound proteins were eluted with a 50 ml gradient of buffer 7 (Table 1) (FIG. 4B, Lane 3 and FIG. 4D, Lane 3). The eluents were pooled and directly loaded onto the PCNA-Agarose column pre-equilibrated with buffer 8 (Table 1) at a flow rate of 1 ml/min. After washing with buffer 8, the bound proteins were eluted with a 50 ml

TABLE 2

Summary of the fitting parameters of the elution peaks of the purified proteins from the PCNA-Agarose column using the EMG model

| Protein | Gradient Range (mM) | Gradient Slope (mM/mL) | τ (mM) | μ (mM) | σ (mM) | τ (mL) | Elution Peak (mM) |
|---|---|---|---|---|---|---|---|
| PIP$^{p21}$-Tus | 80→500 | 32 | 169.4 ± 8.1 | 181.7 ± 1.6 | 29.6 ± 2.0 | 5.3 ± 0.3 | 227 ± 36 |
| Lig1 | 100→815 | 19 | 45.7 ± 1.2 | 219.0 ± 0.6 | 31.0 ± 0.5 | 2.4 ± 0.06 | 246 ± 3 |
| Fen1 | 100→1000 | 27 | 83.5 ± 1.0 | 244.2 ± 1.1 | 21.9 ± 0.8 | 3.1 ± 0.04 | 273 ± 5 |
| p15 | 80→1500 | 44 | 221.0 ± 8.8 | 281.5 ± 3.1 | 38.3 ± 3.0 | 5.0 ± 0.2 | 340 ± 42 |
| Polι | 80→1500 | 46 | 260.5 ± 10.1 | 319.8 ± 1.8 | 20.6 ± 2.5 | 5.7 ± 0.2 | 359 ± 63 |
| Polη | 80→1500 | 48 | 288.5 ± 6.5 | 411.2 ± 2.1 | 77.1 ± 2.4 | 6.0 ± 0.1 | 513 ± 25 |
| Polδ | 80→1500 | 50 | 464.5 ± 23.7 | 393.4 ± 6.0 | 97.3 ± 7.2 | 9.3 ± 0.5 | 534 ± 100 |
| Polκ | 80→1500 | 45 | 297.8 ± 9.2 | 422.1 ± 3.3 | 105.3 ± 3.6 | 6.6 ± 0.2 | 547 ± 30 |

The purified Polδ complex was eluted as a single peak on gel filtration 200 μg with no clear improvement in its purity (FIG. 2B, Lane 6), verifying the functional selectivity of the PCNA-Agarose column.

iii. Purification of FEN1, Lig1, and p15

Next, it was demonstrated that the PCNA-Agarose column can be used as a first step for purifying proteins directly from crude extract. For this purpose, the supernatants from cell pellets of FEN1, Lig1, and p15 were prepared as described above for PCNA. The supernatants were then gradient from 80 mM to 1.5 M NaCl (Buffer 9, Table 1) (FIG. 4B, Lane 5 and FIG. 4D, Lane 5); both Polk and Poli were eluted at ~547 mM and 359 mM NaCl, respectively (FIG. 6A and FIG. 6B, FIGS. 7E and 7H, and Table 2). The peak fractions were collected and dialyzed in dialysis buffer 10 (Table 1) in the presence of SUMO protease to remove the SUMO tag and generate native Polk and Polt. The dialyzed proteins were then passed through a HisTrap column and the untagged proteins were collected in the flow-through fractions (FIG. 4B, Lane 7 and FIG. 4D, Lane 7).

Figure 4F:
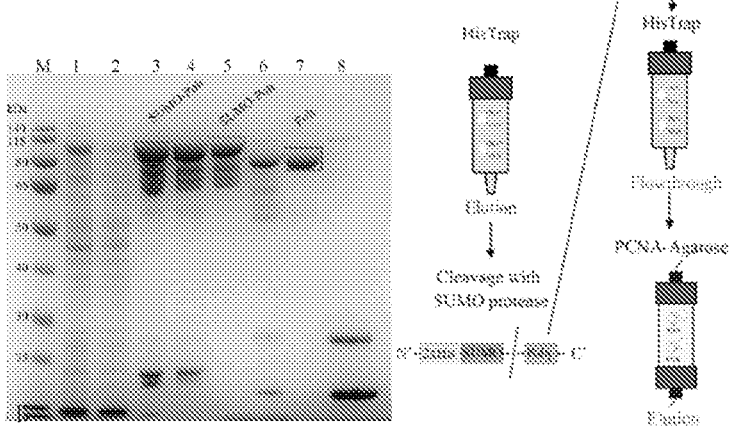
Figure 4F:
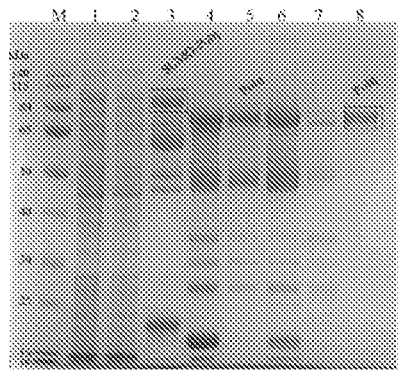
Figure 7F:
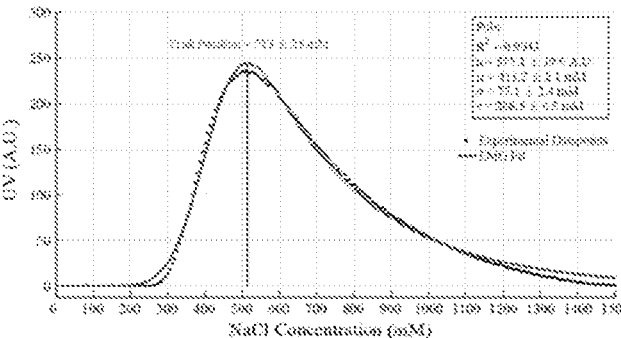

Polk was further loaded onto a gel filtration 200 μg to remove the remaining impurities as shown in FIG. 4B, Lane 9. For Polη, the supernatant was loaded onto a HisTrap column and washed with buffer 5 as described above. The bound protein was eluted with 50 ml of buffer 2 (Table 1) (FIG. 4F, Lane 3). The eluents were collected and dialyzed in dialysis buffer 8 (Table 1) in the presence of SUMO protease to remove the SUMO tag and generate native Polη. The dialyzed protein was then passed through a HisTrap column and the untagged proteins were collected in the flow-through fractions (FIG. 4F, Lane 5). Finally, the flow-through fractions were loaded onto the PCNA-Agarose column, followed by the same washing and elution steps as described above for Polk and Poll (FIG. 4F, Lane 8). Polη was eluted at ~513 mM NaCl (FIGS. 6A, 6B, and 7F, and Table 2).

Example 2: Protein Affinity Columns with non-PCNA-Binding Proteins

Materials and Methods

Figure 5A:
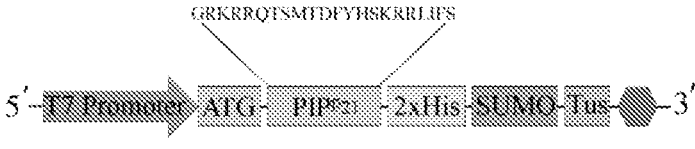
FIGS. 5A, 5B, and 5C show purification of PIPP21-Tus from E. coli.
Figure 5B:
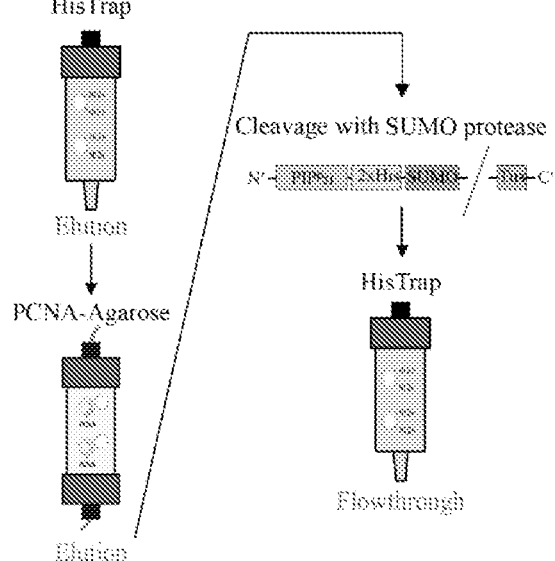

A column similar to that generated as in Example 1 and containing the beads and PCNA described therein was used. All protein fractions were separated on a 10% SDS-PAGE gels and stained with Coomassie blue. PIPp21-TUS was produced in *E. coli* using the construct shown in FIG. 5A, and purification was performed generally following the schematic in FIG. 5B. In this case, a peptide sequence from PIPp21, GRKRRQTSMTDFYHSKRRLIFS (SEQ ID NO: 4), that interacts with PCNA was attached to TUS, a non-PCNA interacting protein, as a strategy to purify TUS.

Results

Purification of PIP$^{p21}$-Tus

Figure 5C:
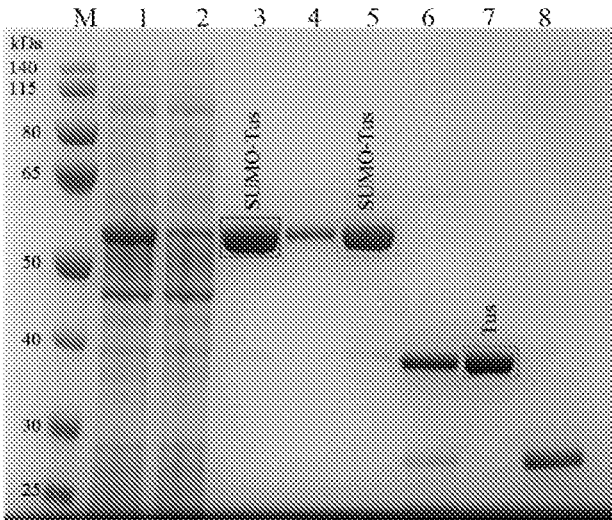

Here, the performance of the PCNA-Agarose column as a tag-affinity purification step was explored, by testing its ability to capture PIP$^{p21}$ motif that was tagged to the *E. coli* replication termination protein Tus that does not bind to PCNA. The supernatant from the cell pellets was mixed with 30 mM imidazole and loaded directly onto a HisTrap column pre-equilibrated with buffer 11 (Table 1). The unbound proteins were washed with buffer 11 and then buffer 12 (Table 1) to reduce the salt concentration. The bound protein was eluted with a gradient from 30 mM to 500 mM imidazole in buffer 13 (Table 1) (FIG. 5C, Lane 3). Fractions that contain PIP$^{p21}$-Tus were combined and diluted to 80 mM NaCl and loaded onto the PCNA-Agarose column pre-equilibrated with buffer 14 (Table 1). The column was then washed with 50 ml of buffer 14, and the protein was eluted with 50 ml of gradient from 80 mM to 500 mM NaCl (FIG. 5C, Lane 5). PIP$^{p21}$-Tus was eluted at ~227 mM NaCl (FIGS. 6A, 6B, and 7A, and Table 2). The peak fractions were collected and dialyzed against buffer 15 (Table 1) in the presence of SUMO protease to remove the PIP$^{p21}$-SUMO tag and generate native Tus. The dialyzed sample was passed through a HisTrap column, and the untagged protein was subsequently collected in the flow-through fractions (FIG. 5C, Lane 7).

Example 3: Analysis of the Elution Chromatograms From the PCNA-Agarose Column Materials and Methods Fitting the Protein Elution Peaks from the PCNA-Agarose Column The binding strength of a given protein to the PCNA-Agarose column was determined by the salt concentration at which the protein was eluted from the column. Two different methods were used for defining and determining this salt concentration. One method relies on empirical calculations while the second method employs a specific model for the elution peak shape. For both methods, protein elution from the column was monitored by the value recorded by the UV detector at 280 nm. The UV absorption was then plotted on the y-axis versus the NaCl concentration (here denoted as 'c') on the x-axis in the gradient region of each chromatogram. Since linear gradients were used for elution, the conversion is readily feasible from the volume in ml to salt concentration in mM on the x-axis, resulting in direct rescaling of the axis.

For the empirical method, no baseline correction was applied. The cumulative elution was calculated up to a concentration by integration as follows:

$$\text{Cumulative Elution } (\%)(c) = \frac{100}{\int_{c_o}^{C_{100}} UV(c)dc} \times \int_{c_o}^{c} UV(c)dc$$

where c represents the current salt concentration, $c_o$ and $c_{100}$ represent the salt concentration at the beginning and at the end of the elution gradient, respectively, and UV (c) represents the measured UV absorption value at the current salt concentration $\partial_c^{C100}UV(c)dc$ represents the total area under the peak and is presented to ensure normalization. For this approach, the median value of each cumulative elution curve was used, i.e., the salt concentration at which 50% of the total protein is eluted, thus permitting the comparison of the elution concentrations.

For the peak modeling method, an Exponentially-Modified Gaussian (EMG) profile was assumed for the elution peaks, as previously described in (Kalambet, et al., Journal of Chemometrics 2011, 25, 352-356; Grushka, Analytical Chemistry 1972, 44, 1733-1738). Before proceeding to the fitting, a baseline subtraction routine was applied using the inbuilt function of the GE Unicorn software. The elution peaks were fitted to the EMG functions as described by:

$$\begin{cases} UV(c; h, \mu, \sigma, \tau) = \frac{h\sigma}{\tau}\sqrt{\frac{\pi}{2}} \exp\left(\frac{1}{2}\left(\frac{\sigma}{\tau}\right)^2 - \frac{c-\mu}{\tau}\right) \text{erfc}\left(\frac{1}{\sqrt{2}}\left(\frac{\sigma}{\tau}\right) - \frac{c-\mu}{\sigma}\right) \\ UV(c; h, \mu, \sigma, \tau) = h\exp\left(-\frac{1}{2}\left(\frac{c-\mu}{\sigma}\right)^2\right)\frac{\sigma}{\tau}\sqrt{\frac{\pi}{2}} \text{erfcx}\left(\frac{1}{\sqrt{2}}\left(\frac{\sigma}{\tau} - \frac{c-\mu}{\sigma}\right)\right) \end{cases}$$

where c represents the current salt concentration, h is the amplitude of the Gaussian distribution which is proportional to the amount of eluted protein, u and o are the mean and the standard deviation of the Gaussian part of the model and t is the relaxation time of the exponential part of the model. Erfc and erfcx are the regular and the scaled complementary error functions, respectively. Both equations mentioned above are perfectly equivalent, but in practice from case to case one may be preferable over the other for the convergence of the fitting algorithm. All peaks were fitted with the above-mentioned function using the cftool package within MATLAB software. Once the fitting parameters h, μ, σand τ were obtained, the main parameter of interest could be determined, namely the mode, i.e., the position of the elution peak maximum as given by:

$$\text{Mode} = \mu - \sigma\sqrt{2}\,\text{erfcxinv}\left(\frac{\tau}{\sigma}\sqrt{\frac{2}{\pi}}\right) + \frac{\sigma^2}{\tau}$$

where erfcxinv is the inverse scaled complementary error function and all the other variables are as defined previously. All parameters ($\mu$, $\sigma$, $\tau$ and the mode) have the same units.

PCNA is known to coordinate the activity of many DNA replication and repair proteins. Thus, it is beneficial to compare the binding strengths of these proteins to PCNA. A binding assay based on chromatography is presented, where the PCNA-Agarose column is used as an analytical tool. The protein of interest was loaded onto the PCNA-Agarose column at low salt concentration followed by extensive washing with a buffer of an equal ionic strength to remove the non-specifically bound proteins. A salt gradient was applied to the column to elute the bound protein of interest. This gradient region of elution in the chromatogram was used for the subsequent analysis. Firstly the values on the x-axis of the chromatogram were converted from volume (ml) or time (min) to salt concentration (mM), by taking advantage of the linear gradient elution mode. The resulting data points, i.e., UV units versus salt concentrations, were analyzed either by the empirical method of cumulative integration or by fitting the peak profile with an EMG model. The defined salt concentration of elution is considered to be a measure of the binding affinity of the protein in question.

In the case of the empirical analysis, the cumulative elution profiles for all the above studied proteins are shown in FIG. 6A. The median value was reported for each protein, i.e., the salt concentration at which half of the total amount of protein is eluted. Three classes of proteins seem to emerge from these analyses: those that eluted at less than 300 mM NaCl constituted of $PIP^P_{21}$-Tus, Lig1, and FEN1; those which eluted between 300 mM and 400 mM NaCl constituted of p15 and Polt; and those that eluted at more than 400 mM NaCl constituted by Pol$\eta$, Pol$\kappa$ and Pol$\delta$. This type of analysis, though easy and informative, has three main limitations: it does not include any baseline correction, and therefore any baseline effect will be amplified by the cumulative integration, it is subjective to the definition chosen for the elution salt concentration (in this case chosen to be the median value), and it does not report any error or uncertainty.

To avoid the limitations of the empirical method, an EMG model was employed for fitting the elution peaks, after performing a baseline correction.

Results

The elution peak profiles for the studied proteins were fitted using the EMG model as described herein (FIGS. 7A-7H) and the resulting parameters of the fit were recorded together with their 95% confidence interval (Table 2). Based on these parameters, the position of the peak maximum together with its 95% confidence interval was calculated for each protein (FIG. 6B). The results are consistent with those calculated by the empirical model, even within the 5% uncertainty limits. This analysis points out that there is at least 150 mM NaCl concentration difference between the proteins that contain a single versus multiple PIP motifs. Using the same EMG analysis, and converting the exponential relaxation of the EMG model from salt concentration to volume by using the elution gradient slope, a relaxation volume of 1-2 column volumes for a column volume of 3-5 ml was estimated (Table 2).

Coupling PCNA with a resin has been employed previously in a limited scope to purify human replication factor C using N-terminus NHS ester coupling (Ohta, et al., J. Biol. Chem. 2002, 277 (43), 40362-40367; Gerik, et al., J. Biol. Chem. 1997, 272 (2), 1256-1262). This type of coupling method may limit the orientation of PCNA and restrict its binding to partner proteins. Furthermore, NHS chemistry is also known to be pH dependent and to react with lysine residues (for reviews on coupling chemistries refer to Koniev, et al., Chemical Society Reviews 2015, 44, 5495-5551). Here, the coupling site was controlled by providing an exogenous cysteine residue instead of the surface-exposed asparagine 107, as described previously (Hedglin, et al., Elife 2013, 2; Hedglin and Benkovic, Biochemistry 2017, 56, 1824-1835), and the altered PCNA was coupled to an agarose column using sulfhydryl-iodoacetic chemistry. Using this PCNA-Agarose column, purified seven different proteins were successfully purified, thus establishing PCNA as a broad tag-free affinity chromatography method. Moreover, the competence of the PCNA-Agarose column as a tag-dependent affinity chromatography method was demonstrated by fusing a peptide containing the PIP motif of human p21 protein into *E. coli* Tus.

Given the number of proteins that interact with PCNA, the PCNA-Agarose column can have a real impact on the purification of proteins involved in, but not restricted to, DNA replication, repair and recombination, and also cellular signaling. The purified proteins may also be selected according to their properly folded form at least from the perspective of their interaction with PCNA. The PCNA-Agarose column can also be extended beyond human PCNA given that DNA clamps are present in many species and are highly conserved (Strzalka and Ziemienowicz, Annals of Botany 2011, 107, 1127-1140; Hedglin, et al., Cold Spring harbor Perspectives in Biology 2013, 5). This extension is also reinforced by the design described herein, in which the exogenous cysteine can be easily introduced by mutagenesis, eliminating any topological and structural requirements for the selected clamp.

The use of the PCNA-Agarose column as an analytical tool to measure the relative strength of the interaction between PCNA and its binding partners was also explored. In the case of proteins involved in the maturation of Okazaki fragments, it was found that Pol$\delta$ interacts most strongly with PCNA, followed by FEN1 and then by Lig1 (FIGS. 6A and 6B, and Table 2). This order of affinity is not accidental since it coincides with the order of recruitment of these proteins by PCNA. In the case of TLS polymerases, Pol$\kappa$ and Pol$\eta$ exhibited similar binding strengths as Pol$\delta$ to PCNA, while Polt was situated closer to maturation proteins of the Okazaki fragment FEN1 and Lig1 (FIGS. 6A and 6B, and Table 2). Polt has only one PIP motif, Pol$\kappa$ has two PIP motifs, while Pol$\eta$ has three PIP motifs (Masuda, et al., Nucleic Acids Res. 2015, 43, 7898-7910; Hishiki, et al., J. Biol. Chem. 2009, 284, 10552-10560; Hedglin, et al., Proc. Natl. Acad. Sci. USA 2016, 113, E1777-E1786) and Pol$\delta$ contains three PIP motifs (Brunning and Shamoo, Structure 2004, 12, 2209-2219; Hedglin, et al., Proc. Natl. Acad. Sci. USA 2016, 113, E1777-E1786). A clear separation of more than 150 mM NaCl between the elution of proteins that contain only one PIP motif and those that comprise multiple PIP motifs was observed. Given the strength of the interaction of Pol$\kappa$, there is an open possibility that it might contain a previously unidentified PIP motif. It is also possible that other domains can exhibit and stabilize Pol$\kappa$'s interactions even more efficiently than PIP motifs. One previous study shows that the interaction between TLS polymerases and non-mono-ubiquitylated PCNA is very weak and transient (Masuda, et al., Nucleic Acids Res. 2015, 43, 7898-7910). However, the present study shows that these interactions are in fact strong, since a significant amount of TLS polymerases could be purified using the PCNA-Agarose column.

Example 4: Coupling PCNA to a Surface Via Non-Covalent Interactions

Materials and Methods
i. Plasmid Construction

The sequence encoding for human PCNA (accession no. NP002583) was amplified by PCR from the IDT-synthesized gene described above and cloned into the multiple cloning site 1 (MCS1) of a pETDuet-1 Amp+ (Novagen) plasmid using the Gibson cloning protocol. An AviTag™ (encoding for the amino acid sequence GLNDIFEAQKIEWHE (SEQ ID NO: 6)) sequence and a sequence encoding for a double His-tag (8XHis-GGGS linker-6XHis (SEQ ID NO: 7), denoted in FIG. 8A as 2XHis8-6) were inserted at the N-terminus by PCR. Glycine-Serine linkers were introduced in-between the two tags (a GGGS linker (SEQ ID NO: 8)), as well as in-between PCNA and the two tags (a GS linker) to ensure the exposure of these tags during the purification. pBirAcm plasmid containing the BirA gene was extracted from AVB99 cells (purchased from Avidity™) by a standard Miniprep plasmid extraction kit. The sequence encoding the BirA enzyme was amplified by PCR from the pBirAcm and cloned into the MCS2 of the same pETDuet-1 Amp+ (Novagen) plasmid where PCNA was cloned into the MCS1. This plasmid is denoted from here onward as pAviPCNA-BirA (FIG. 8A). This plasmid ensures the co-expression of the N-terminal AviTag™-tagged PCNA that is ready for biotinylation and of the enzyme BirA that will transfer the biotin molecule covalently to the AviTag™-tagged PCNA (FIG. 8B).

ii. Expression of Biotinylated PCNA pAviPCNA-BirA was transformed into BL21 (DE3) *E. coli* expression strain (Novagen) by heat shock protocol and plated on Amp+selection LB agar (VWR) media. A single colony was inoculated in LB media supplemented with 100 μg/ml Ampicillin and grown overnight to saturation at 37° C. 4 liters of 2xYT (Teknova) media supplemented with the same amount of antibiotic was inoculated from the overnight pre-culture and grown at 37° C. When the cell growth reached an $OD_{600}$ of 0.8, expression was induced by the addition of 0.5 mM IPTG (isopropyl β-D-1-thiogalactopyranoside) and incubation continued for additional 4 hours at 37° C. At the time of induction, 50 mM D-Biotin solution (Invitrogen) was also added in the culture to a final concentration of 75 μM. Cells were harvested by centrifugation at 6000xg for 15 min and then re-suspended in 5 ml per 1 g of wet cells in Lysis Buffer [50 mM Tris pH (7.5), 500 mM NaCl, 20 mM Imidazole, 10 mM β-Mercaptoethanol, 1 mM PMSF, 5% Glycerol and one EDTA free protease inhibitor cocktail tablet/50 ml (Roche, UK)] with stirring for 40 min.

iii. Immobilizing Biotinylated PCNA to Avidin-Agarose Resin

Biotin-Avidin interaction is one of the strongest known non-covalent interactions in nature and in particular in biological systems. The strength of this interaction is characterized by a dissociation constant in the femto-molar range, with a dissociation rate in the order of tens of hours (Duan, et al., Nature Nanotechnology2012, 7 (6), 401-407. This stability makes this interaction ideal for protein immobilization to non-cellular surfaces.

Figure 8C:
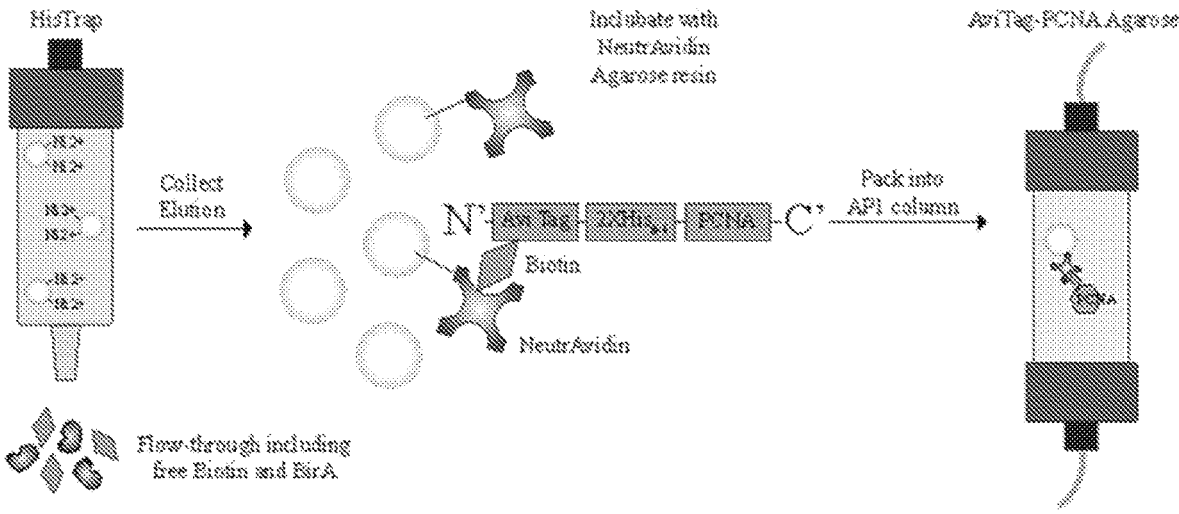

The resin used for the Biotin-labeled PCNA capturing was High Capacity NeutrAvidin™ Agarose Resin (Thermo Scientific). The buffer used for protein binding, washing and elution from this column was Buffer C [50 mM Tris-HCl (pH 7.5), 500 mM NaCl, 10 mM β-Mercaptoethanol and 5% Glycerol]. The buffers used for protein binding, washing and elution from the His Trap column were Buffer A [50 mM Tris-HCl (pH 7.5), 500 mM NaCl, 10 mM β-Mercaptoethanol, 5% Glycerol and 20 mM Imidazole] and Buffer B [50 mM Tris-HCl (pH 7.5), 500 mM NaCl, 10 mM β-Mercaptoethanol, 5% Glycerol and 750 mM imidazole]. The protocol used for AviTag-PCNA coupling to the agarose resin is illustrated in FIG. 8C.

Figure 8D:
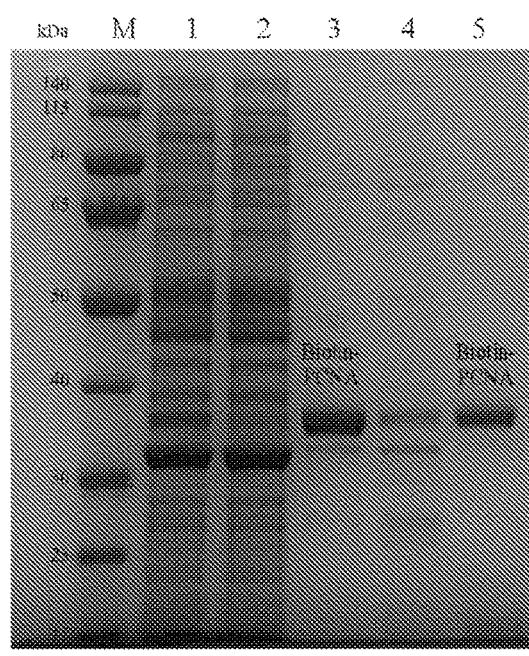

The soluble fraction of the cell lysates containing Avi-Tag™-His-PCNA (FIG. 8D, lane1) was applied to HisTrap affinity column that was pre-equilibrated with Buffer A. The protein fusion was eluted from the column with a 15 CV linear gradient from 20 mM to 750 mM Imidazole of Buffer B. The protein fusion eluted in a peak centered at ~200 mM Imidazole (lane 3 in FIG. 8D). This fraction can be used for coupling immediately or stored at –80° C. for later use or shipping purposes.

The protein fusion eluted from the HisTrap column was then incubated with the NeutrAvidin™ Agarose Resin for 2 hours at 4° C. The flow-through (lane 4 in FIG. 8D) was collected by centrifugation. 2.5 ml of Buffer C are then added to the resin to produce a 50% slurry. This PCNA-coupled resin was then packed into a column; we denoted this column as AviTag™-PCNA-Agarose. The storage buffer used for all the proteins used in this study was Storage Buffer [50 mM Tris-HCl (pH 7.5), 150 mM NaCl, 1 mM Dithiothreitol (DTT) and 5% Glycerol].

iv. Purification of Lig1 through the PCNA-biotin Cavidin-Agarose Column

Figure 9A:
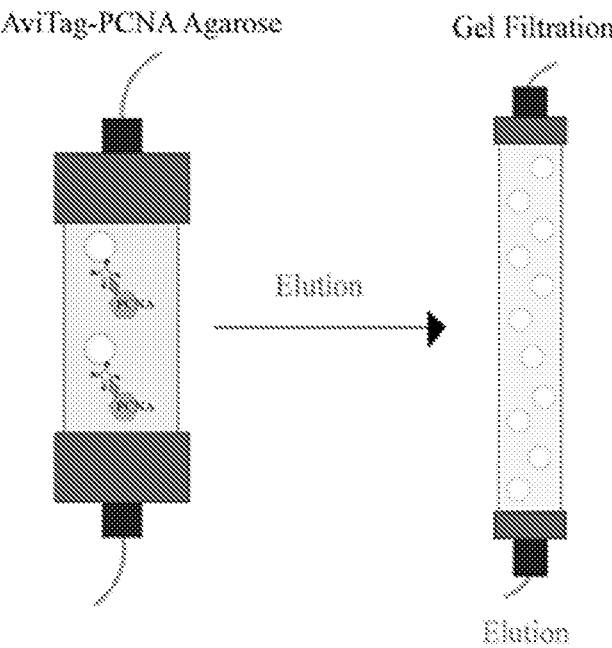
FIGS. 9A and 9B show purification of human recombinant Lig1 from *E. coli* using the AviTag™-PCNA-Agarose column.

The selectivity power of the PCNA-Agarose column is illustrated in the purification of Lig1 from *E. coli* extract. The buffers used for Lig1 binding, wash and elution from this column were buffer D [50 mM Tris-HCl (pH 7.5), 80 mM NaCl, 10 mM β-Mercaptoethanol and 5% Glycerol] and buffer E [50 mM Tris-HCl (pH 7.5), 1000 mM NaCl, 10 mM β-Mercaptoethanol and 5% Glycerol]. The schematic representation of the purification of Lig1 through the PCNA-biotin.avidin-Agarose column is shown in FIG. 9A.

The soluble fraction of the cell lysate containing Lig1 (lane 1 in FIG. 9B) was applied to the 2.5 ml PCNA-Agarose column that was pre-equilibrated with buffer D. The column was then washed with 10 CV of Buffer D. The protein was eluted from the column with a 15 CV linear gradient of Buffer E from 80 mM to 1000 mM NaCl. The protein eluted in a peak centered at ~237 mM NaCl (lane 3 in FIG. 9B).

The fractions containing Lig1 were concentrated to 1.5 ml using 30 kDa cut-off spin concentrators and applied to a Superdex 200 pg size-exclusion column that was pre-equilibrated with Storage Buffer. The pure fractions were selected (lane 3 in FIG. 9B) and concentrated to 2.5 ml using 30 kDa cut-off spin concentrators. Two PD-10 desalting columns were equilibrated three times with Storage Buffer. The concentrated proteins were then passed through the PD-10 columns for rapid exchange of the buffer to Storage Buffer and then further concentrated to 1 ml using 10 kDa cut-off spin concentrators.

The elution profile of Lig1 from the PCNA-Agarose column was fitted to an EMG profile as described in the Methods section. The fitting result and parameters are presented in FIG. 9C. From these fitting parameters we determined the mode of the elution profile of Lig1 from the PCNA-Agarose column to be 237±12 mM NaCl.

SDS-PAGE Analysis

For SDS-PAGE analysis, 5 μl of all the studied fractions were used. After mixing with 10 μl of 5× electrophoresis sample buffer, the samples were heated up for 5 min at 96° C., and then loaded onto 10% SDS-PAGE gel. The gels were stained with staining solution (40% methanol, 20% glacial acetic acid, 40% water and Coomassie Brilliant Blue G-250)

while heating in a microwave for 1 min and de-stained with water while heating for 10 min in a microwave.

Results

The amount of bound AviTag™-PCNA was quantified by measuring the absorbance at 280 nm using NanoDrop spectrophotometer (Thermo Scientific); the extinction coefficient was considered to be 64290 M-1 cm-1 for the AviTag™-PCNA homotrimer. The yield of the bound AviTag™-PCNA was ~19 mg of protein bound to 2.5 ml of settled resin, resulting in a binding capacity of 7.6 mg/ml. This yield was estimated as described above for the other coupling methods for PCNA (FLAG, Strep, etc.). The bound fraction of AviTag™-PCNA can be visualized in lane 5 in FIG. 8D. It is worth mentioning that the binding capacity of the High Capacity NeutrAvidin™ Agarose Resin is ~8 mg/ml, meaning that AviTag™-PCNA was coupled to the High Capacity NeutrAvidin™ Agarose Resin with ~95% theoretical efficiency.

The slurry was then packed into an AP-1 glass column (Waters) and washed with 20 CV of Buffer C to release any non-specifically-bound PCNA. Human Ligase 1 (Lig1) was purified as described above but using PCNA-Agarose column that was prepared through AviTag™-PCNA immobilization on High Capacity NeutrAvidin™ Agarose rather than the aforementioned coupling by the N107C PCNA to SulfoLink resin.

Figure 9B:
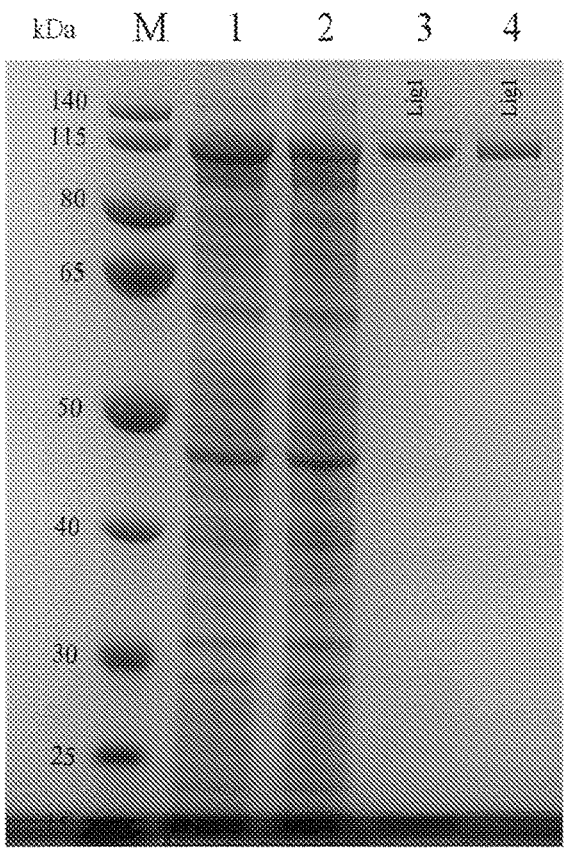
Figure 9C:
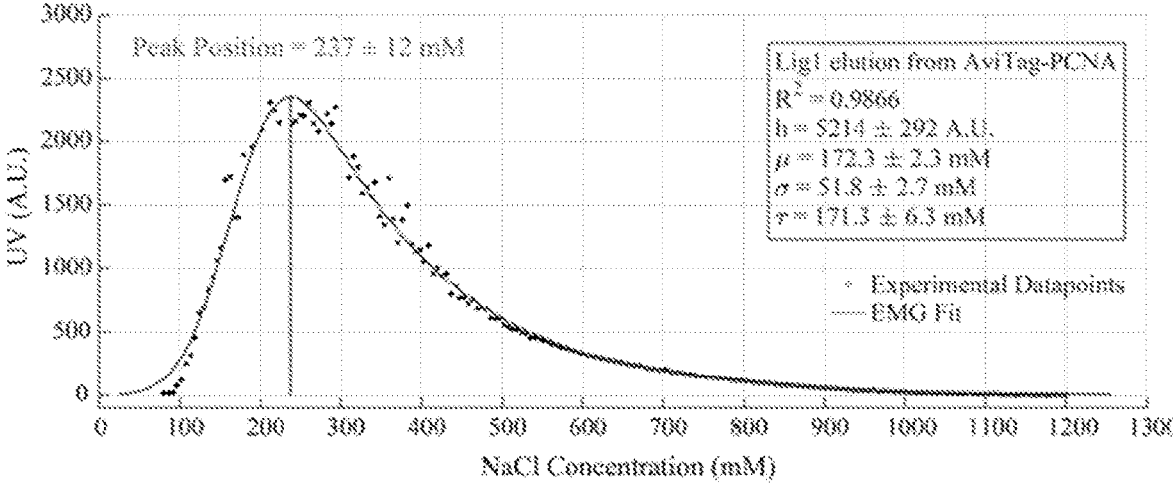
FIG. 9C shows fitting of the elution peak of Lig1 from the PCNA-Agarose column by the EMG model. The values of the EMG parameters are shown in the inset table with their 95% confidence interval. The goodness of fit is indicated by the R2 value. The vertical line terminating at the peak of the curve represents the position of the maximum of the elution peak as calculated from the fitting parameters as described in the Methods section. This value together with its 95% confidence interval is also reported above the peak.

The purification results of Lig1 over PCNA-Agarose columns were consistent with each other regardless whether PCNA N107C is coupled to SulfoLink resin (FIGS. 3D and 7B) or AviTag™-PCNA is immobilized on NeutrAvidin™ Agarose (FIGS. 9B and 9C). Previous studies showed low and inconsistent expression and solubility of BirA when the protein was expressed from the commercial pBirAcm plasmid (Li, et al., *Biotechnol. Lett.*, 34:1629-1635 (2012). In the current work through the design of the expression constructs and conditions consistent expression of considerable amount of soluble BirA was achieved (an intense band on SDS-PAGE above the 30 kDa marker present in the soluble fraction of the lysates; lane 1 in FIG. 8D). This expression and solubility of BirA allowed for efficient in vivo biotinylation of the AviTag-tagged fusions, which together with the removal of the free unbound biotin by the first Ni-NTA (nitrilotriacetic acid) step yielded almost complete capturing of the fusions by the avidin resin.

This demonstrate that both N107C- and AviTag™-PCNA-Agarose columns performed equally well. Nerveless, AviTag™-PCNA immobilization on High Capacity NeutrAvidin™ Agarose is much easier and faster experimentally, especially by removing the stringent requirement of freshly purified and reduced PCNA, i.e., the AviTag™-PCNA provides perfect solution to shipping it along with the resin, which will allow the users to perform the resin-coupling step quickly and at ease.

In conclusion, the PCNA-Agarose column is an ideal tool for the purification and analysis of PCNA-interacting proteins and peptides, even for the PIP$^{P21}$-tagged proteins and peptides that do not naturally interact with PCNA. The PCNA-Agarose column also has many applications that are beneficial for laboratories working in protein sciences, especially those exploring DNA replication, recombination and repair, and cellular signaling.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An affinity system comprising: a carrier, a sliding clamp protein, and (a) a linker; wherein an internal residue of the protein is conjugated to the carrier via a covalent linkage comprising the linker or (b) non-covalent linkage, wherein the protein is conjugated to the carrier via one or more non-covalent interactions.

2. The affinity system of claim 1, wherein the covalent linkage comprises a linker having the structure -X—Y-Ra-Formula I wherein: X contains between 3 and 90 atoms; Y is —NHC(O)—; —C(O)NH—; —C(O)O—; —OC(O)—; —O—; —NH—NHC(O)—; —OC(O)NH—; —NHC(O) O—; —C(O)—; —OC(O)O—; —S($=O_2$)$_2$—; —S($=$O)—; —S—; —N$=$N—; —N$=$CH—; a bond, and Ra is a thioether, a substituted triazole, a carbamate, oxime ether, hydrazone, a carbonyl, imine, sulfonamide, azo, dialkyl dialkoxysilane, diaryl dialkoxysilane, orthoester, acetal, aconityl, p-thiopropionate, phosphoramidate, trityl, vinyl ether, polyketal, or a combination thereof.

3. The affinity system of claim 2, wherein X is a substituted alkyl; unsubstituted alkyl; substituted alkylene; unsubstituted alkylene; a polyether; unsubstituted alkynyl; or a combination thereof.

4. The affinity system of claim 1, wherein the linker comprises a thioether, optionally, both a thioether and an amide.

5. The affinity system of claim 1, wherein the non-covalent linkage is selected from the group consisting of electrostatic interactions, hydrogen bonding interactions, metal coordination, physical adsorption, host-guest interactions, hydrophobic interactions, van der Waals interactions, magnetic interactions, and dipole-dipole interactions or combinations thereof.

6. The affinity system of claim 5 (i) further comprising: (a) polyhistidine; (b) one or more molecule pairs selected from the group consisting of (i) biotin and a biotin-binding compound and (ii) FLAG-epitope and an anti-Flag antibody, or (c) one or more glycine serine linkers; or (ii) wherein the non-covalent linkage comprises affinity interactions, and optionally, wherein the system further comprises one or more glycine-serine linkers.

7. The affinity system of claim 1, further comprising (a) biotin, and a biotin-binding compound, wherein the biotin-binding compound is selected from the group consisting of avidin, streptavidin and neutravidine, (b) FLAG-epitope and an anti-FLAG antibody, (c) polyhistidine and nickel (II) nitriloacetic acid, (d) a hydrophobic molecule selected from the group consisting of a hydrophobic polymer and a small organic moiety comprising an alkyl group wherein the small organic moiety is a butyl, hexyl or phenyl group, and combinations thereof.

8. The affinity system of claim 1, wherein the internal residue is: (a) not present in its corresponding position in a wild-type state of the protein; (b) incorporated into the protein via site-directed mutagenesis; (c) a natural amino acid, non-natural occurring amino acid, or a combination thereof; (d) a cysteine; and/or (e) a fusion protein comprising a bait.

9. The affinity system of claim 1, wherein the protein is: (a) a fusion protein comprising a bait; (b) a homo-multimeric or hetero-multimeric protein; (c) a recombinant protein; (d) a fusion protein or (e) wherein the protein is from eukaryotes, archaea, bacteria, viruses, or a combination thereof.

10. The affinity system of claim 9, wherein the protein is from a *Homo sapiens, Macaca fascicularis, Macaca nemestrina, Rhinopithecus bieti, Gorilla gorilla, Nomascus, leucogenys, Mandrillus leucophaeus, Neovison vison, Ovis aries, Bos taurus, Rattus norvegicus, Oryza sativa, Mus musculus, Saccharomyces cerevisiae, Saccharolobus solfataricus, Pyrococcus furiosus, Archaeoglobus fulgibus, Thermococcus kodakarensis, Leishmania donovani, Sulfurisphaera tokodaii, Murine leukemia virus, Haloferax volcanii, Penaeus vannamei, Ricinus communis, Thermococcus gammatolerans, Escherichia coli* or a combination thereof.

11. The affinity system of claim 1, wherein: (a) the protein is from a *Homo sapiens*, (b) the protein is a proliferating cell nuclear antigen (PCNA); or (c) the protein comprises a peptide sequence according to SEQ ID NO:1 or SEQ ID NO:5.

12. The affinity system of claim 1, further comprising a PCNA fusion protein comprising, PCNA, a polyhistidine domain, and a biotin-binding domain.

13. The affinity system of claim 12, wherein the biotin-binding domain comprises SEQ ID NO:6 and the polyhistidine domain comprises hexahistidine; optionally, (a) further comprising at least one linker comprising SEQ ID NO:10, or (b) wherein the at least one linker is SEQ ID NO:9 or SEQ ID NO: 8.

14. The affinity system of claim 1, wherein the carrier comprises a polysaccharide such as agarose and/or the affinity system is a purification column.

15. A method of removing a target molecule from a sample containing the target molecule, the method comprising: contacting the sample to the affinity system of claim 1, wherein the target molecule binds to the protein.

16. The method of claim 15, wherein the target molecule is a target protein,
   optionally, wherein the target protein is an enzyme or a
   non-enzymatic protein.

17. The method of claim 16, wherein the target protein comprises a PCNA interaction peptide (PIP) or the target protein is: (a) a protein that naturally interacts with sliding clamp proteins; (b) a protein that does not naturally interact with sliding clamp proteins and contains one or more sliding clamp protein interacting peptides; (c) a fusion protein; (d) obtained by from a cell that has been genetically engineered to express the target protein.

18. The method of claim 17, wherein the PIP comprises SEQ ID NO:4.

19. The system of claim 2, wherein X comprises between 3 and 85 atoms.

20. The system of claim 7, wherein the hydrophobic polymer is selected from the group consisting of polymethacrylate, polyorthoester, polysebacic anhydride, unmodified poly(lactic acid), polycaprolactone.

21. The system of claim 2, wherein (i) the substituted triazole is alkyne+azide formed by "click"-chemistry, (ii) the carbamate is amine+hydroxy using diimidazole carbonyl; or isocyanate+hydroxy, (iii) oxime ether is carbonyl+aminooxy, (iv) the hydrazone carbonyl+hydrazide, (iv) the carbonyl is a ketone), (v) the imine is carbonyl+amine, (vi) the sulfonamide is sulfonyl chloride+amine, or (vii) the azo is aromatic diazonium and anilines or phenols.

22. The system of claim 2, wherein (i) X does not have between 80 and 85 atoms, or between 75 and 80 atoms; (ii) X does not contain poly(ethylene glycol); (iii) X does not contain unsubstituted alkylene and poly(ethylene glycol); (iv) Ra is not a substituted triazole; (v) Ra is not a substituted succinimide; or (vi) Formula I does not include a combination of (i)-(v).

23. The system of claim 19, wherein X comprises between 3 and 80 atoms.

24. The system of claim 19, wherein X comprises between 3 and 70 atoms.

25. The system of claim 19, wherein X comprises between 3 and 60 atoms.

26. The system of claim 19, wherein X comprises between 3 and 50 atoms.

27. The system of claim 19, wherein X comprises between 3 and 40 atoms.

28. The system of claim 19, wherein X comprises between 3 and 30 atoms.

29. The system of claim 19, wherein X comprises between 3 and 20 atoms.

30. The system of claim 19, wherein X comprises 10, 11, 12, 13, 14, or 15 atoms.

\* \* \* \* \*

SEQUENCE LISTING

```
<160> NUMBER OF SEQ ID NOS: 10

<210> SEQ ID NO 1
<211> LENGTH: 261
<212> TYPE: PRT
<213> ORGANISM: Homo sapiens

<400> SEQUENCE: 1

Met Phe Glu Ala Arg Leu Val Gln Gly Ser Ile Leu Lys Lys Val Leu
1               5                   10                  15

Glu Ala Leu Lys Asp Leu Ile Asn Glu Ala Cys Trp Asp Ile Ser Ser
            20                  25                  30

Ser Gly Val Asn Leu Gln Ser Met Asp Ser Ser His Val Ser Leu Val
        35                  40                  45

Gln Leu Thr Leu Arg Ser Glu Gly Phe Asp Thr Tyr Arg Cys Asp Arg
    50                  55                  60

Asn Leu Ala Met Gly Val Asn Leu Thr Ser Met Ser Lys Ile Leu Lys
65                  70                  75                  80

Cys Ala Gly Asn Glu Asp Ile Ile Thr Leu Arg Ala Glu Asp Asn Ala
                85                  90                  95

Asp Thr Leu Ala Leu Val Phe Glu Ala Pro Asn Gln Glu Lys Val Ser
            100                 105                 110

Asp Tyr Glu Met Lys Leu Met Asp Leu Asp Val Glu Gln Leu Gly Ile
            115                 120                 125
```

-continued

```
Pro Glu Gln Glu Tyr Ser Cys Val Val Lys Met Pro Ser Gly Glu Phe
    130             135             140

Ala Arg Ile Cys Arg Asp Leu Ser His Ile Gly Asp Ala Val Val Ile
145             150             155             160

Ser Cys Ala Lys Asp Gly Val Lys Phe Ser Ala Ser Gly Glu Leu Gly
            165             170             175

Asn Gly Asn Ile Lys Leu Ser Gln Thr Ser Asn Val Asp Lys Glu Glu
                180             185             190

Glu Ala Val Thr Ile Glu Met Asn Glu Pro Val Gln Leu Thr Phe Ala
            195             200             205

Leu Arg Tyr Leu Asn Phe Phe Thr Lys Ala Thr Pro Leu Ser Ser Thr
    210             215             220

Val Thr Leu Ser Met Ser Ala Asp Val Pro Leu Val Val Glu Tyr Lys
225             230             235             240

Ile Ala Asp Met Gly His Leu Lys Tyr Tyr Leu Ala Pro Lys Ile Glu
            245             250             255

Asp Glu Glu Gly Ser
            260
```

```
<210> SEQ ID NO 2
<211> LENGTH: 1271
<212> TYPE: DNA
<213> ORGANISM: Homo sapiens

<400> SEQUENCE: 2
gcgtagcaga gtggtcgttg tctttctagg tctcagccgg tcgtcgcgac gttcgcccgc      60
tcgctctgag gctcctgaag ccgaaaccag ctagactttc ctccttcccg cctgcctgta     120
gcggcgttgt tgccactccg ccaccatgtt cgaggcgcgc ctggtccagg gctccatcct     180
caagaaggtg ttggaggcac tcaaggacct catcaacgag gcctgctggg atattagctc     240
cagcggtgta aacctgcaga gcatggactc gtcccacgtc tctttggtgc agctcaccct     300
gcggtctgag ggcttcgaca cctaccgctg cgaccgcaac ctggccatgg gcgtgaacct     360
caccagtatg tccaaaatac taaaatgcgc cggcaatgaa gatatcatta cactaagggc     420
cgaagataac gcggatacct ggcgctagt atttgaagca ccaaaccagg agaaagtttc     480
agactatgaa atgaagttga tggatttaga tgttgaacaa cttggaattc agaacagga     540 gtacagctgt gtagtaaaga tgccttctgg tgaatttgca cgtatatgcc gagatctcag     600
ccatattgga gatgctgttg taatttcctg tgcaaaagac ggagtgaaat tttctgcaag     660
tggagaactt ggaaatggaa acattaaatt gtcacagaca agtaatgtcg ataaagagga     720
ggaagctgtt accatagaga tgaatgaacc agttcaacta acttttgcac tgaggtacct     780
gaacttcttt acaaaagcca ctccactctc ttcaacggtg acactcagta tgtctgcaga     840
tgtacccctt gttgtagagt ataaaattgc ggatatggga cacttaaaat actacttggc     900
tcccaagatc gaggatgaag aaggatctta ggcattctta aaattcaaga aaataaaact     960
aagctctttg agaactgctt ctaagatgcc agcatatact gaagtctttt ctgtcaccaa    1020
atttgtacct ctaagtacat atgtagatat tgttttctgt aaataaccta tttttttctc    1080
tattctctgc aatttgttta agaataaag tccaaagtca gatctggtct agttaaccta    1140
gaagtatttt tgtctcttag aaatacttgt gattttata atacaaaagg gtcttgactc    1200
taaatgcagt tttaagaatt gtttttgaat ttaaataaag ttacttgaat ttcaaaaaaa    1260
aaaaaaaaaa a                                                        1271
```

<210> SEQ ID NO 3
<211> LENGTH: 1319
<212> TYPE: DNA
<213> ORGANISM: Homo sapiens

<400> SEQUENCE: 3

```
aacgcggcgc agggtgagag cgcgcgcttg cggacgcggc ggcattaaac ggttgcaggc      60
gtagcagagt ggtcgttgtc tttctaggtc tcagccggtc gtcgcgacgt tcgcccgctc     120
gctctgaggc tcctgaagcc gaaaccagct agactttcct ccttcccgcc tgcctgtagc     180
ggcgttgttg ccactccgcc accatgttcg aggcgcgcct ggtccagggc tccatcctca     240
agaaggtgtt ggaggcactc aaggacctca tcaacgaggc ctgctgggat attagctcca     300
gcggtgtaaa cctgcagagc atggactcgt cccacgtctc tttggtgcag ctcaccctgc     360
ggtctgaggg cttcgacacc taccgctgcg accgcaacct ggccatgggc gtgaacctca     420
ccagtatgtc caaaatacta aaatgcgccg gcaatgaaga tatcattaca ctaagggccg     480
aagataacgc ggataccttg gcgctagtat ttgaagcacc aaaccaggag aaagtttcag     540
actatgaaat gaagttgatg gatttagatg ttgaacaact tggaattcca gaacaggagt     600
acagctgtgt agtaaagatg ccttctggtg aatttgcacg tatatgccga gatctcagcc     660
atattggaga tgctgttgta atttcctgtg caaaagacgg agtgaaattt tctgcaagtg     720
gagaacttgg aaatggaaac attaaattgt cacagacaag taatgtcgat aaagaggagg     780
aagctgttac catagagatg aatgaaccag ttcaactaac ttttgcactg aggtacctga     840
acttctttac aaaagccact ccactctctt caacggtgac actcagtatg tctgcagatg     900 tacccccttgt tgtagagtat aaaattgcgg atatgggaca cttaaaatac tacttggctc     960
ccaagatcga ggatgaagaa ggatcttagg cattcttaaa attcaagaaa ataaaactaa    1020
gctctttgag aactgcttct aagatgccag catatactga agtcttttct gtcaccaaat    1080
ttgtacctct aagtacatat gtagatattg ttttctgtaa ataacctatt tttttctcta    1140
ttctctgcaa tttgtttaaa gaataaagtc caaagtcaga tctggtctag ttaacctaga    1200
agtatttttg tctcttagaa atacttgtga ttttttataat acaaaagggt cttgactcta    1260
aatgcagttt taagaattgt ttttgaattt aaataaagtt acttgaattt caaacatca     1319
```

<210> SEQ ID NO 4
<211> LENGTH: 22
<212> TYPE: PRT
<213> ORGANISM: Homo sapiens

<400> SEQUENCE: 4

```
Gly Arg Lys Arg Arg Gln Thr Ser Met Thr Asp Phe Tyr His Ser Lys
1               5                   10                  15

Arg Arg Leu Ile Phe Ser
            20
```

<210> SEQ ID NO 5
<211> LENGTH: 274
<212> TYPE: PRT
<213> ORGANISM: Artificial Sequence
<220> FEATURE:
<223> OTHER INFORMATION: Synthetic peptide

<400> SEQUENCE: 5

```
Met Gly Ser Ser His His His His His His Ser Gln Asp Met Phe Glu
1               5                   10                  15
```

-continued

```
Ala Arg Leu Val Gln Gly Ser Ile Leu Lys Lys Val Leu Glu Ala Leu
            20              25              30

Lys Asp Leu Ile Asn Glu Ala Cys Trp Asp Ile Ser Ser Ser Gly Val
            35              40              45

Asn Leu Gln Ser Met Asp Ser Ser His Val Ser Leu Val Gln Leu Thr
    50              55              60

Leu Arg Ser Glu Gly Phe Asp Thr Tyr Arg Cys Asp Arg Asn Leu Ala
65              70              75              80

Met Gly Val Asn Leu Thr Ser Met Ser Lys Ile Leu Lys Cys Ala Gly
            85              90              95

Asn Glu Asp Ile Ile Thr Leu Arg Ala Glu Asp Asn Ala Asp Thr Leu
            100             105             110

Ala Leu Val Phe Glu Ala Pro Cys Gln Glu Lys Val Ser Asp Tyr Glu
            115             120             125

Met Lys Leu Met Asp Leu Asp Val Glu Gln Leu Gly Ile Pro Glu Gln
    130             135             140

Glu Tyr Ser Cys Val Val Lys Met Pro Ser Gly Glu Phe Ala Arg Ile
145             150             155             160

Cys Arg Asp Leu Ser His Ile Gly Asp Ala Val Val Ile Ser Cys Ala
            165             170             175

Lys Asp Gly Val Lys Phe Ser Ala Ser Gly Glu Leu Gly Asn Gly Asn
            180             185             190

Ile Lys Leu Ser Gln Thr Ser Asn Val Asp Lys Glu Glu Glu Ala Val
            195             200             205

Thr Ile Glu Met Asn Glu Pro Val Gln Leu Thr Phe Ala Leu Arg Tyr
    210             215             220

Leu Asn Phe Phe Thr Lys Ala Thr Pro Leu Ser Ser Thr Val Thr Leu
225             230             235             240

Ser Met Ser Ala Asp Val Pro Leu Val Val Glu Tyr Lys Ile Ala Asp
            245             250             255

Met Gly His Leu Lys Tyr Tyr Leu Ala Pro Lys Ile Glu Asp Glu Glu
            260             265             270

Gly Ser
```

```
<210> SEQ ID NO 6
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 6

Gly Leu Asn Asp Ile Phe Glu Ala Gln Lys Ile Glu Trp His Glu
1               5               10              15
```

```
<210> SEQ ID NO 7
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 7

His His His His His His His His Gly Gly Gly Ser His His His His
1               5               10              15

His His
```

-continued

```
<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 8

Gly Gly Gly Ser
1

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

Gly Gly Gly Gly Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: REPEAT
<222> LOCATION: (1)..(5)
<223> OTHER INFORMATION: The sequence is repeated 'n' times, where 'n'
      is not defined.

<400> SEQUENCE: 10

Gly Gly Gly Gly Ser
1               5
```